United States Patent
Morgan

(10) Patent No.: US 10,580,321 B1
(45) Date of Patent: Mar. 3, 2020

(54) SYSTEM AND METHOD FOR CONVERSION OF RANGE DISTANCE VALUES TO PHYSICAL POSITION BY ACTUATION OF A TACTILE FEEDBACK WHEEL

(71) Applicant: James P. Morgan, West Lebanon, NH (US)

(72) Inventor: James P. Morgan, West Lebanon, NH (US)

(*) Notice: Subject to any disclaimer, the term of this patent is extended or adjusted under 35 U.S.C. 154(b) by 0 days.

(21) Appl. No.: 16/159,495

(22) Filed: Oct. 12, 2018

Related U.S. Application Data

(60) Provisional application No. 62/571,765, filed on Oct. 12, 2017.

(51) Int. Cl.
| | |
|---|---|
| *G09B 21/00* | (2006.01) |
| *G06F 3/01* | (2006.01) |
| *G01S 15/08* | (2006.01) |
| *A61H 3/06* | (2006.01) |
| *A61H 23/02* | (2006.01) |

(52) U.S. Cl.
CPC .......... *G09B 21/003* (2013.01); *A61H 3/061* (2013.01); *A61H 23/0245* (2013.01); *G01S 15/08* (2013.01); *G06F 3/016* (2013.01); *A61H 2003/063* (2013.01); *A61H 2201/0153* (2013.01); *A61H 2201/1635* (2013.01); *A61H 2201/1692* (2013.01); *A61H 2201/5048* (2013.01)

(58) Field of Classification Search
None
See application file for complete search history.

(56) References Cited

U.S. PATENT DOCUMENTS

| | | | |
|---|---|---|---|
| 6,198,395 B1 | 3/2001 | Sussman | |
| 6,298,010 B1 | 10/2001 | Ritz et al. | |
| 6,486,784 B1 | 11/2002 | Beckers | |
| 7,755,744 B1 | 7/2010 | Leberer | |
| 7,788,032 B2 | 8/2010 | Moloney | |
| 7,855,657 B2 | 12/2010 | Doemens et al. | |
| 8,803,699 B2 | 8/2014 | Foshee et al. | |
| 2007/0016425 A1* | 1/2007 | Ward | A61H 3/061 |
| | | | 704/271 |
| 2010/0182134 A1 | 7/2010 | Perkins | |
| 2013/0220392 A1* | 8/2013 | Gassert | A61H 3/061 |
| | | | 135/66 |
| 2017/0178465 A1* | 6/2017 | Lashina | G08B 1/08 |

* cited by examiner

*Primary Examiner* — Carlos Garcia
(74) *Attorney, Agent, or Firm* — Loginov & Associates, PLLC; William A. Loginov

(57) ABSTRACT

An Environmental Navigation Aid is provided, and can be a rechargeable, portable, handheld device that can convert environmental information, such as distance to a target object, into tactile values for presentation to a user's palm or fingers by way of a tactile feedback wheel. The nature of the target object composition can be factored into the behavior of the feedback wheel. The Environmental Navigation Aid can be paired with a wireless charging dock that can also serve as a homing beacon when the handheld device is pointed at the changing dock. Stand-alone homing beacons for additional orientation referencing tasks can be added to an Environmental Navigation Aid as a system. The Environmental Navigation Aid is designed to assist the blind in perception of the world around them.

18 Claims, 19 Drawing Sheets

SYSTEM AND METHOD FOR CONVERSION OF RANGE DISTANCE VALUES TO PHYSICAL POSITION BY ACTUATION OF A TACTILE FEEDBACK WHEEL

FIELD OF THE INVENTION

This invention relates to assistive devices for the blind that convert environmental range distance to tactile feedback for the user.

BACKGROUND OF THE INVENTION

The blind have long sought new devices to assist in their daily activities. The ubiquitous cane has been the standard mobility tool for the blind for centuries. The advantages of the cane are offset by the disadvantages of its physical nature and reach. Scanning for objects and people can be slow and cumbersome due to the care a user must take when searching with a long physical stick. Other tools to convey environmental ranging information to the blind typically employ a variety of vibration systems, which have little sense of absolute position and are inherently numbing to the user's skin. The ideal system for ranging should utilize non-contact detection and employ a reasonably precise feedback system that is suited for long term use. Such an ideal system should provide the user with information about the composition of what it is pointed at, address indication of distance from user to target, and be useful for identification of edge parameters.

SUMMARY OF THE INVENTION

The Environmental Navigation Aid (ENA) of the present disclosure overcomes disadvantages of the prior art by providing indication of edge parameter detection, distance to an object, and/or a basic understanding of solidity and/or complexity of the object composition. This information can be collected by a non-contact ranging device, which can be in the form of an ultrasonic range finder. The collected information can be conveyed to the user by a tactile feedback unit, which can include a variable-location tactile feedback unit that can include a tactile feedback wheel.

In an embodiment, an ENA can include a range finding unit that measures a distance between an object and the ENA, and a tactile feedback unit with at least one tactile feedback wheel, wherein the tactile feedback unit moves along an exterior of the ENA to indicate the distance between the object and the ENA. The at least one tactile feedback wheel can include teeth arranged radially around the wheel. The at least one tactile feedback wheel can have a central axis that can be perpendicular to a direction of travel of the tactile feedback unit. The at least one tactile feedback wheel can include at least two tactile feedback wheels. The central axis of a first wheel can be perpendicular to the central axis of a second wheel. The range finding unit can use ultrasound to measure the distance between the object and the ENA. The range finding unit can include a speaker and at least one microphone. The tactile feedback unit can provide information to the user about the surface texture of an object. The ENA can include a homing unit that can make a noise in response to a predetermined stimulus. The predetermined stimulus can be an ultrasonic tone produced by an ENA charging unit. The location of the tactile feedback unit can be directly proportional to the distance between the object and the ENA. The location of the tactile feedback unit can be exponentially proportional to the distance between the object and the ENA.

In an embodiment, a homing system for a blind user can include at least one homing unit with at least one microphone capable of detecting a predetermined stimulus, and a speaker that emits an audible tone in response to the predetermined stimulus. The predetermined stimulus can be an ultrasonic tone. The predetermined stimulus can be produced by a range finding ENA. The at least one homing unit can include at least two homing units, and each homing unit can emit a different audible tone.

A method for a blind user to navigate an environment can include: obtaining a range finding ENA; pointing the ENA at an object in the environment; and determining, based on the location of a tactile feedback unit on the ENA, a distance between the object and the ENA. The method can include determining, based on small movements of the tactile feedback unit, the texture of a surface of the object. The method can include feeling the location of wheels on the tactile feedback unit. Feeling the location of the wheels can include feeling the location of teeth on the wheels.

BRIEF DESCRIPTION OF THE DRAWINGS

The invention description below refers to the accompanying drawings, of which.

DETAILED DESCRIPTION

Figure 1:
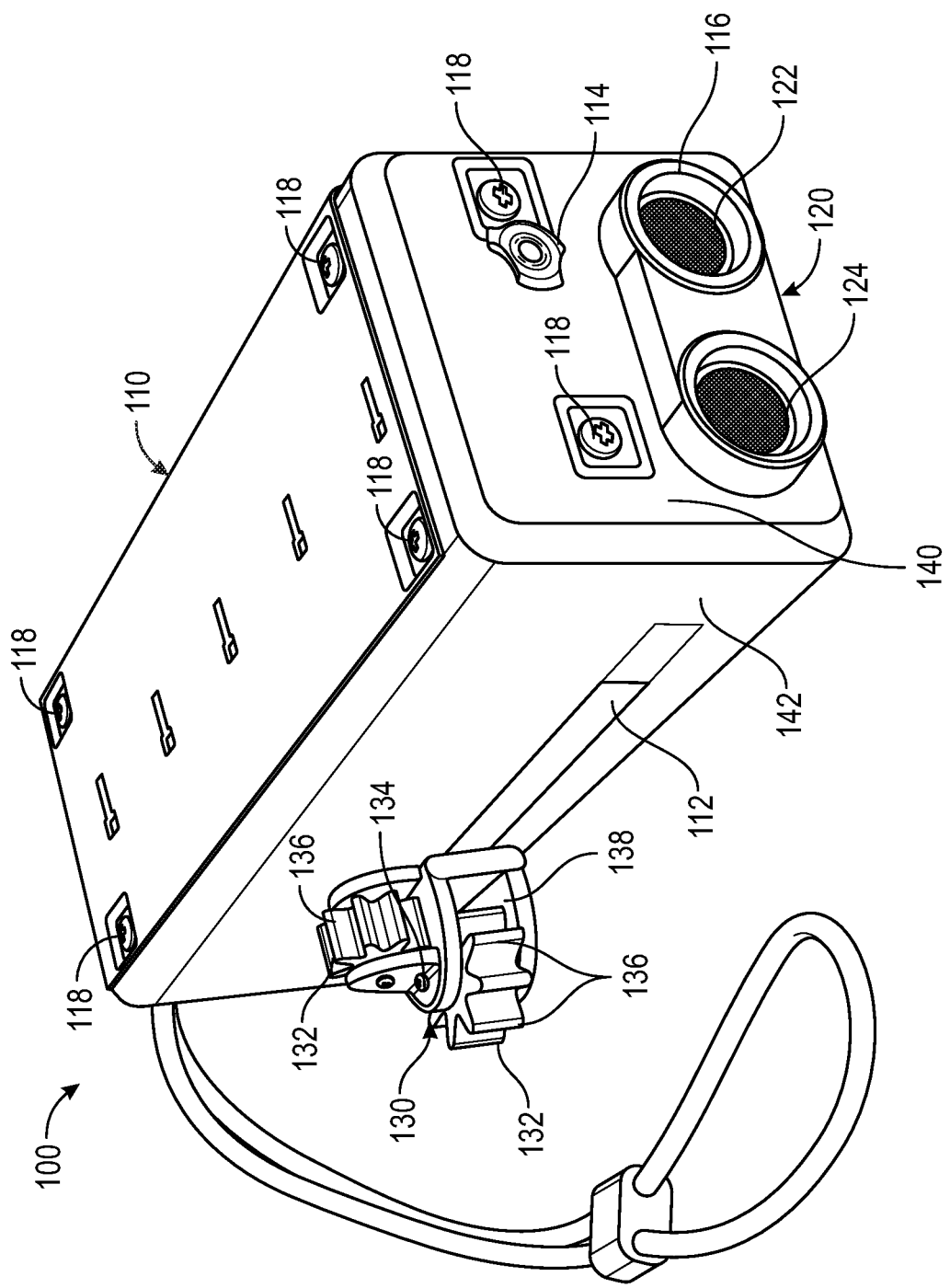
FIG. 1 is a perspective view of an exemplary Environmental Navigation Aid (ENA) hand unit, according to an illustrative embodiment.

The Environmental Navigation Aid (ENA) of the present disclosure can collect information about an environment through non-contact information collection which can include an ultrasonic range finder. An ultrasonic range finder operates above the hearing range of humans and pet animals such as cats, dogs, and birds. The device can perform well indoors and outdoors and is unaffected by falling snow, rain, fog, or air pollution. The ENA can provide information regarding distance to an object that it is pointed at by a user. This distance information can be conveyed to the user by a tactile feedback unit. This tactile feedback unit can be comprised of one or more tactile feedback wheels positioned on the ENA so that a user may receive the feedback in a number of ways.

The tactile feedback unit can have a variable location on the ENA. The tactile feedback unit can move through a range of locations on the ENA to provide information to a user regarding distance to an object. The position on the ENA of a tactile feedback unit can be a scaled representation of the real distance to the target object. A tactile feedback unit can glide across a user's palm, thumb, or finger, where a user can feel the position of the tactile feedback unit with a good amount of accuracy. Additionally, due to the nature of sound and microprocessor data manipulation, the tactile feedback unit can move quickly back and forth over a small distance to indicate that an object is made of a soft or complex series of surfaces, such as cloth or clutter. This is called scatter. The more complex the surface, the longer the throw, or movement of the tactile feedback unit, and the more varied the pattern of the scatter can be. A smooth hard wall can result in a steady position of the tactile feedback unit that can include minor, or a complete lack of, scatter. Clothing can present a small degree of scatter and a cluttered desk can yield a large degree of scatter. A user can become skilled in interpreting the parameters of an object, as well as the nature of the surface of the object, based on the motion of the tactile feedback wheels through experience.

Distance data can be gathered from an ultrasonic sensor that can use sonar to determine distance to an object. This distance data can be processed by a microprocessor that can include one or more modules that can eliminate noise and/or can scale the data to move the tactile feedback unit within the physical range of motion for the tactile feedback unit. The tactile feedback unit, which can include one or more tactile feedback wheels, can be moved along a path by a servomotor. The ENA device can be powered by a battery. The internal components of an ENA device can fit into a shell that can be held in an average human hand.

A tactile feedback wheel can be in the shape of a small toothed gear that can roll smoothly over the skin but can still be easily felt, especially the actual placement on the palm or other portion of a user's hand. That absolute position of the tactile feedback unit on the ENA can translate into the distance to a target object that the ENA device is pointed at.

A charging base station that utilizes wireless charging capabilities can be paired to the hand held ENA. The ENA can be recharged by placing it on the charging base station. The charging base station can use a wall power adapter as source power. The ENA can use a microprocessor to manage charging and detect when an ENA is placed in its tray. Additionally, the charging base can act as a homing beacon. When the onboard microphone detects the ultrasonic output of the ENA, a chime or other tone can sound. The distance at which it can detect the ENA can be modifiable by a small user serviceable door in front of the microphone.

FIG. 1 is a perspective view of an exemplary ENA hand-held unit, according to an illustrative embodiment. An ENA unit 100 can include an outer case 110, a range finding unit 120, and a tactile feedback unit 130. In an exemplary embodiment, the ENA 100 can have a front side 140 and a tactile side 142, however, it is specifically contemplated that the exterior shape of the ENA 100 can be varied without departing from the spirit and scope of the present disclosure. Descriptions of specific sides of the ENA 100 are provided herein only to facilitate descriptions of possible uses and components of the ENA 100, and should not be construed as required for the ENA 100. By way of non-limiting example, the exterior case 110 of the ENA 100 could be cylindrical, in the shape of a flashlight, or other ergonomic designs that can be configured for ease of holding and use, and without particular sides or corners.

The outer case 110 can include a track 112, so that exterior components of the tactile feedback unit 130 can move along the track 112. The outer case 110 can include a visibility enhancing light 114. Visibility enhancing light 114 can be blue, or other colors. Visibility enhancing light 114 can be a high-powered LED that can blink as a visibility aid. Visibility enhancing light 114 can help sighted people be aware of a blind user of an ENA who might be waving an ENA through space, and the visibility enhancing light can help to reduce the likelihood of collisions with sighted individuals. The outer case 110 can include a protective shield 116 that can protect components of the range finding unit 120 from impact. The outer case 110 can be provided with attachment points 118, so that, for example, screws can be used to hold portions of the outer case together. One or more panels of the outer case 110 can be unattached and removed to allow access to the interior components of the ENA.

The range finding unit 120 can be an ultrasound system that can include a speaker 122 and at least one microphone 124, as will be understood by one skilled in the art. The range finding unit 120 can measure a distance between the range finding unit 120 and an object in front of the range finding unit. The range finding unit 120 can be in communication with a microprocessor in the ENA 100, so that the range finding unit 120 can provide ranging data collected by the range finding unit 120 to the microprocessor.

The tactile feedback unit 130 can move along the track 112 to communicate a distance between the range finding unit 120 and an object in front of the range finding unit. A position of the tactile feedback unit 130 at one end of the track 112 can indicate that an object is close, and a position of the tactile feedback unit at the other end of the track can indicate that the object is far away, or that there is no object in front of the range finding unit. In an embodiment, the track 112 can span laterally along at least a portion of the length between the front side 140 and the back side. In an embodiment, the tactile feedback unit 130 can move towards the front side 140 to indicate that the object in front of the range finding unit is more distant from the range finding unit 120, and the tactile feedback unit 130 can move towards the back side to indicate that the object in front of the range finding unit 120 is closer to the range finding unit. In an embodiment, the tactile feedback unit can move towards the front side 140 to indicate that the object in front of the range finding unit is closer to the range finding unit 120, and the tactile feedback unit 130 can move towards the back side to indicate that the object in front of the range finding unit is more distant from the range finding unit 120. In an embodiment, the user can select whether the front end of the track 112 indicates closer or farther away. Track 112 is shown in FIG. 1 as being oriented along a straight line that is parallel to the sides of the ENA 100 and off-center (closer to one side than the other), however, it is specifically contemplated that in various embodiments, the track 112 can be centered down the middle of one side of the ENA, can be at a non-parallel angle to the sides of the ENA 100, can be curved along a flat side of the ENA 100, can be curved around a curved surface of an ENA, such as the curves of an ergonomically-shaped ENA 100, or other possible configurations.

The tactile feedback unit 130 can include at least one tactile feedback wheel 132. The tactile feedback wheel 132 can spin on an axle 134. Axle 134 can be oriented perpendicular to the length of the track 112, so that the feedback wheel 132 can roll along the direction of travel of the tactile feedback unit 130. The axle 134 can be at the central axis of the tactile feedback wheel 132. The feedback wheel 132 can roll across the palm, finger, or other portion of the user as the tactile feedback unit 130 moves along the length of the track 112. The feedback wheel can reduce friction or irritation felt by the user because the feedback wheel can roll across the user's skin instead of rubbing the user's skin as the feedback unit 130 moves along the track 112.

The feedback wheel 132 can be in the shape of a cog, or gear, with multiple teeth 136 extending outwards from the feedback wheel 132. The teeth 136 can increase the sensation felt by the user as the feedback unit 130 travels along the track 112 and the feedback wheels 132 roll across the user along the direction of travel. Each tooth 136 can slightly indent the skin of the user, thereby providing more precise tactile information to the user when compared to a wheel without teeth or a feedback unit without a wheel. The teeth 136 can also help to ensure that the wheel 132 rolls along the skin of the user instead of sliding along the user as the feedback unit 130 travels. The sensation felt by the user from a series of teeth 136 that can slightly indent the skin at a series of single locations can allow the user to feel the communicated distance information with increased precision. The series of slight indentions at a series of locations can also allow the user to maintain sensitivity without irritation over an extended period of use as compared to a tactile feedback unit that slides or rubs along the skin of the user. Compared to a wheel without teeth, the smaller points of contact created by the teeth 136 can also reduce the amount of contact and friction experienced by the user from the tactile feedback unit 130, which can further improve sensitivity, precision, and long-term comfort for the user.

The tactile feedback unit 130 can include multiple feedback wheels 132 that can spin on axles 134. The axles 134, and the central axes of the wheels 132, can be oriented at different angles that can each be perpendicular to the length of the track 112. The axles 134, and the central axes of the wheels, can be perpendicular to each other. As shown in the illustrative example of FIG. 1, multiple feedback wheels 132 can be positioned at different angles relative to each other, and can each roll along the direction of travel of the tactile feedback unit 130. The tactile feedback unit 130 can include at least one fender 138 that can partially cover a wheel 132. The fender 138 can limit the contact between a user and a wheel 132 to a predetermined portion of the feedback wheel 132. This can decrease the number of teeth 136 in contact with the user at a time, can limit friction between the skin of the user and the side of the feedback wheel 132, and can help the feedback wheel to spin freely due to the lack of contact between the user and the side of the wheel.

Figure 2:
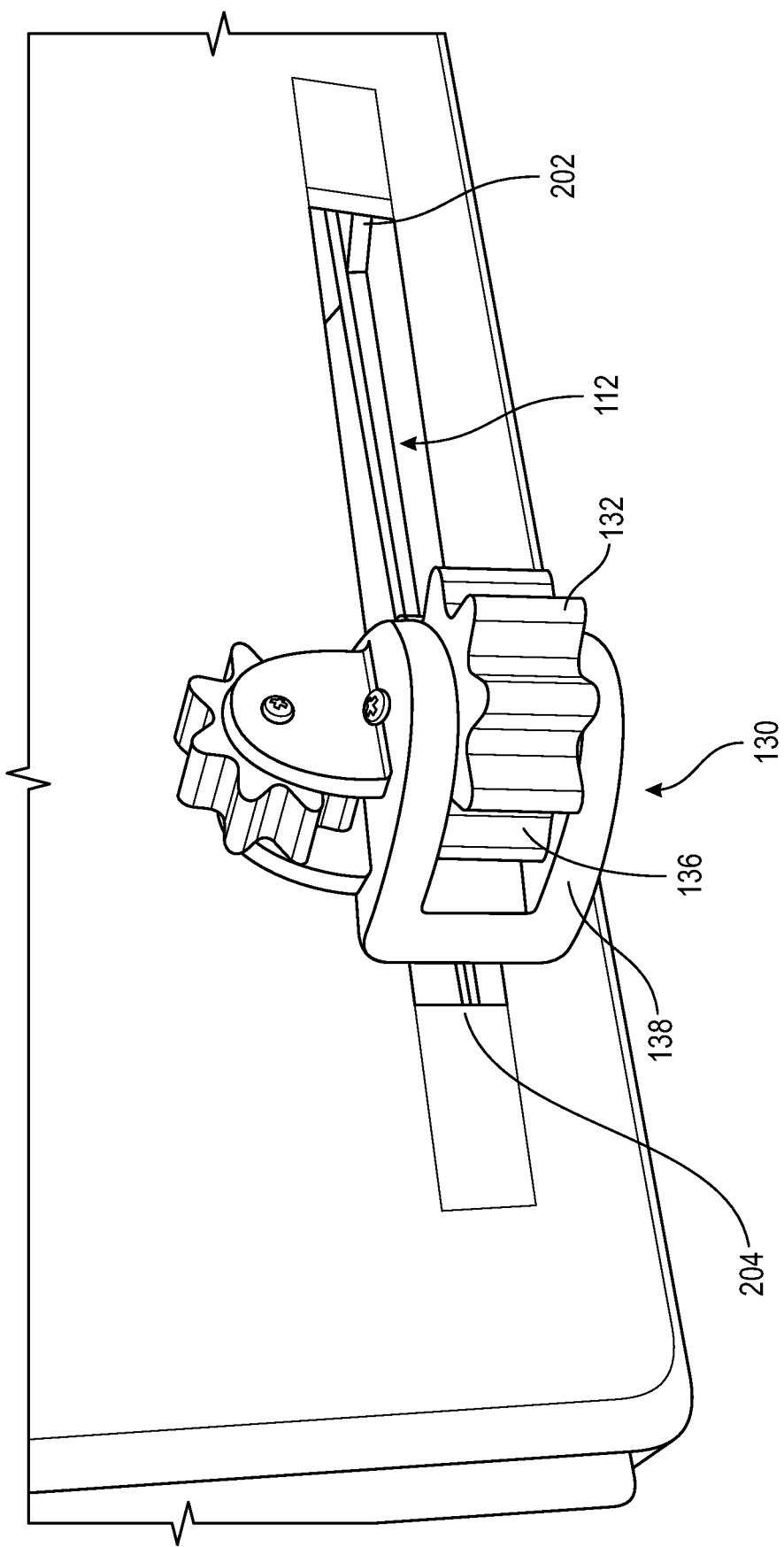
FIG. 2 is a perspective view of an exemplary tactile feedback unit of the ENA of FIG. 1 showing primary and secondary tactile feedback wheels, according to an illustrative embodiment.

FIG. 2 is a perspective view of an exemplary tactile feedback unit of the ENA of FIG. 1 showing primary and secondary tactile feedback wheels, according to an illustrative embodiment. A tactile feedback unit 130 can communicate information about an object in front of the ENA 100 by traveling back and forth along the length of a track 112. A track 112 can have a distal end 202 that can be the portion of the track that can be nearest to the front side of the ENA, and a track 112 can have a proximal end 204 that can be the portion of the track that is farthest from the front side of the ENA. In alternate embodiments, the tactile feedback unit can move from side to side, or along a curved path, or other movements to communicate information about an object.

Figure 3A:
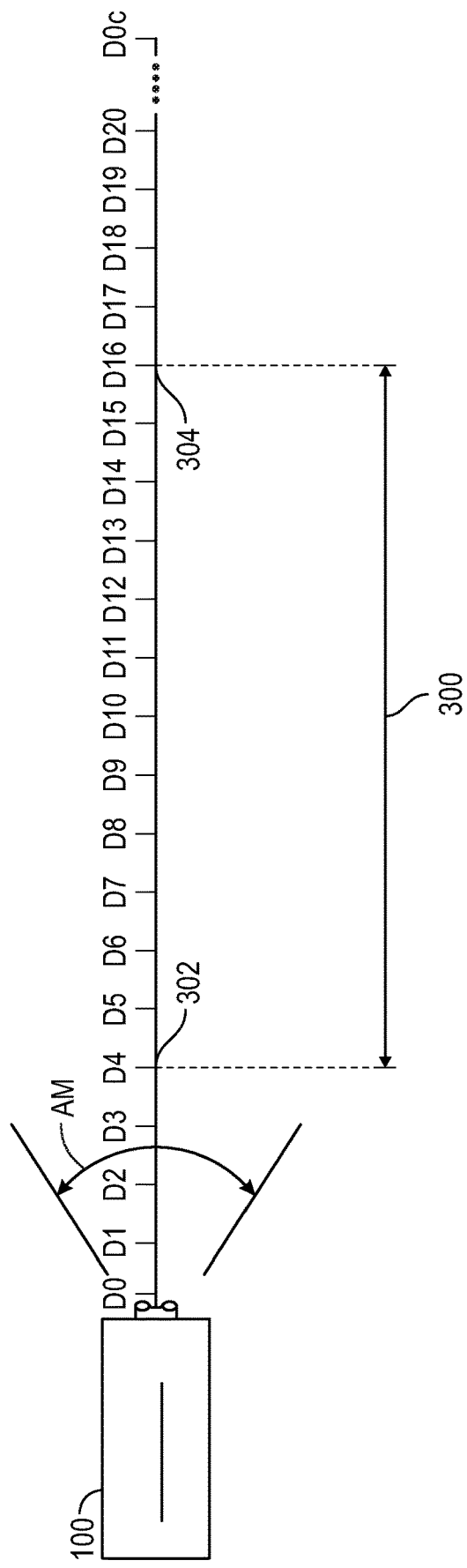
FIG. 3A is a schematic view of an ENA with a distance range, according to an embodiment.

FIG. 3A is a schematic view of an ENA with a distance range, according to an embodiment. The ENA 100 (not drawn to scale) is shown with distances D0 to D20 from the front side 140 of the ENA, with D0 being no distance from the ENA 100. The ENA 100 can have a distance range 300 that can be defined by a minimum distance from the ENA 302 and a maximum distance from the ENA 304. In the example shown in FIG. 3A, the minimum distance 302 is D4 and the maximum distance 304 is D16, however this example is provided only to assist in explaining the operation of the ENA and is not intended to represent actual distances measured by the ENA. In an embodiment, the minimum distance 302 can be D0 or another distance, the minimum distance can be adjustable, and/or the maximum distance can be adjustable. The ENA 100 can indicate that an object is at the minimum distance 302 (D4) or closer than the minimum distance (at a distance from D0 to D4) by moving the tactile feedback unit 130 to the proximal end 204 of the track 112. The ENA 100 can indicate that an object is at the maximum distance 304, farther than the maximum distance, or that no object is in front of the ENA 100 (at a distance from D16 to D∞) by moving the tactile feedback unit to the distal end 202 of the track 112. In alternate embodiments, the proximal end 204 can indicate that the object is distant, and the distal end 202 can indicate that the object is near. In various embodiments, the user may be able to select whether a distant object is indicated by the tactile feedback unit being at the proximal end or the distal end of the track. Although a near object can be indicated by the tactile feedback unit being located at the proximal end 204 of the track 112 or at the distal end 202 of the track 112, depending on the embodiment and/or depending an election by the user, for convenience and clarity the near object will be described as being indicated at the proximal end 204 throughout this application, however, it should be clear that either relationship is specifically contemplated. The ENA 100 can have an angle of measurement AM. Objects that fall within this range of measurements can be reported to the user by the tactile feedback unit. In an embodiment, the angle of measurement AM can be adjustable. The angle of measurement AM can be adjusted by adjusting the protective shroud 116 to limit the width of an area an ultrasonic speaker broadcasts, and/or the width of an area the microphone detects. In various embodiments, the shroud can be adjusted by extending the shroud, or using a longer or narrower shroud.

In an embodiment, the position of the tactile feedback unit along the track can be directly proportional to the position of the object within the distance range, so that the distance of an object that is at a measured percentage of the distance range can be indicated by the ENA by positioning the tactile feedback unit 130 at the same percentage of the track length. The corresponding relationship between the distance of the object as a percentage of the distance range and the location of the tactile feedback unit as a percentage of the track length can be the same regardless of the location of the object within the distance range. In other words, there can be a fixed ratio between the object distance and the location of the tactile feedback unit.

Figure 3B:
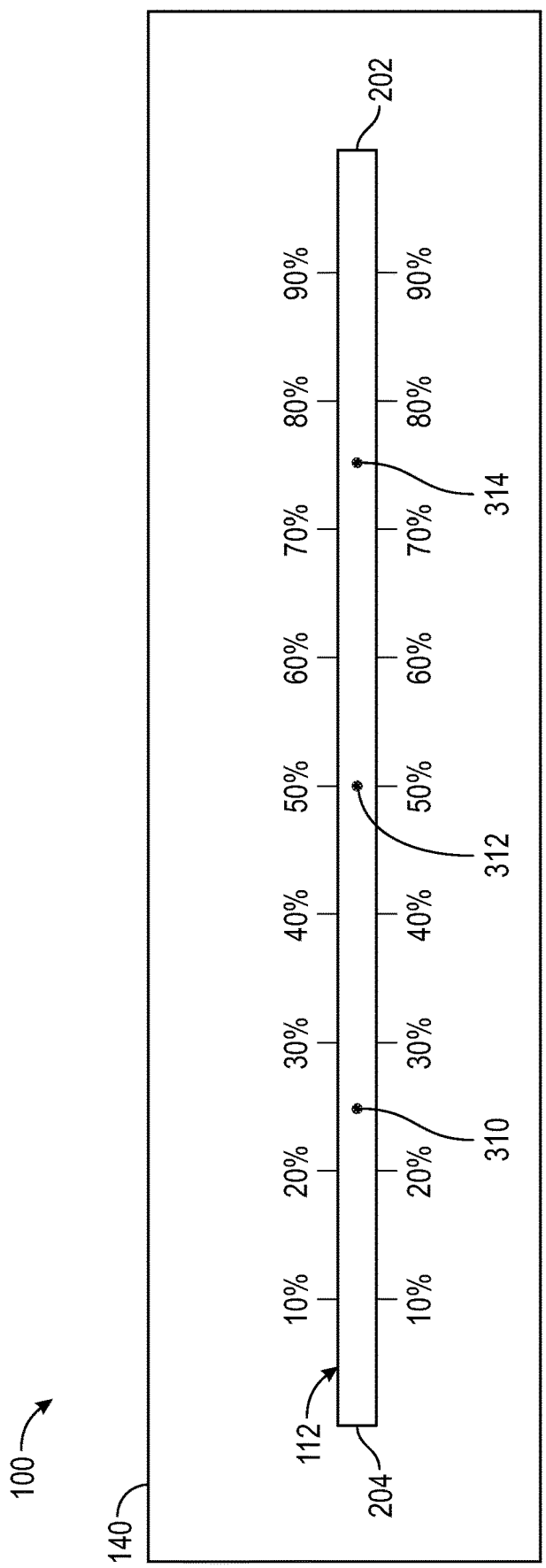
FIG. 3B is a schematic view of an ENA track with proportional distances indicated, according to an embodiment.

FIG. 3B is a schematic view of an ENA track with proportional distances indicated, according to an embodiment. The length of the track 112 between the proximal end 204 and the distal end 202 can represent the distance range of the ENA. The percentage of the track length is indicated above the track 112, and the percentage of the distance range indicated by the tactile feedback unit at a given location along the track is indicated below the track 112. As shown, the percentages are the same. The ENA 100 can indicate the distance of an object within the distance range by moving the tactile feedback unit 130 to a location along the track 112 that is proportional to the distance of the object within the distance range, so that the farther away an object within the distance range is located, the farther the tactile feedback unit 130 moves to the distal end 202 of the track 112. Referring to FIGS. 3A and 3B, an object that is at D7, which is 25% of the distance range 300 would be indicated on the ENA 100 by the tactile unit (not shown) being positioned at position 310, which is 25% of the track length. An object that is at D10, which is at 50% of the distance of the distance range 300 would be indicated on the ENA 100 by the tactile feedback unit being positioned at position 312, which is at 50% of the track length. An object that is at D13, which is 75% of the distance range would be indicated on the ENA 100 by the tactile feedback unit being positioned at position 314, which is at 75% of the track length.

In an embodiment, the position of the tactile feedback unit along the track 112 can be exponentially related to the position of the object within the distance range, so that movement of an object that is closer to the ENA can be indicated by a larger movement of the tactile feedback unit, while a similar movement of an object that is farther from the ENA can be indicated by a smaller movement of the tactile feedback unit. In an embodiment, the relationship between the position of the tactile feedback unit along the track and the position of the object within the distance range can be defined by a polynomial function, so that movement of an object that is closer to the ENA can be indicated by a larger movement of the tactile feedback unit, while a similar movement of an object that is farther from the ENA can be indicated by a smaller movement of the tactile feedback unit.

Figure 3C:
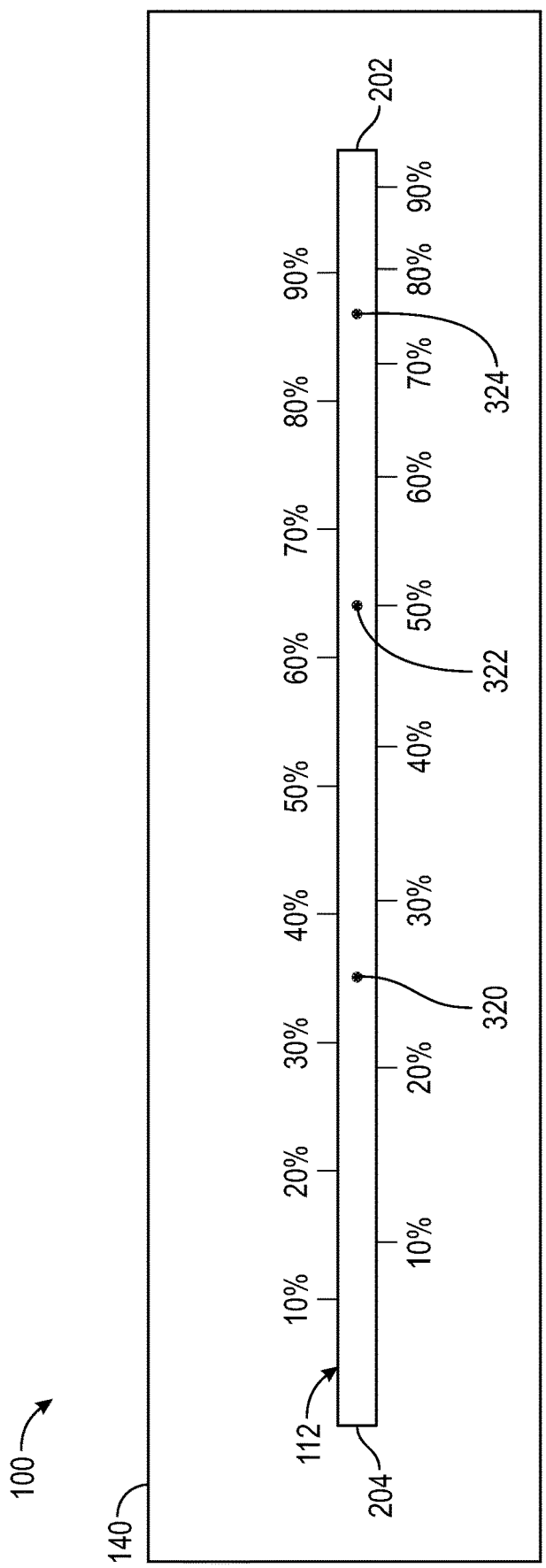
FIG. 3C is a schematic view of an ENA travel path with an exponential relationship for distances indicated, according to an embodiment.

FIG. 3C is a schematic view of an ENA travel path with an exponential relationship for distances indicated, according to an embodiment. The length of the track 112 between the proximal end 204 and the distal end 202 can represent the distance range of the ENA. The percentage of the track length is indicated above the track 112, and the percentage of the distance range indicated by the tactile feedback unit at a given location along the track is indicated below the track 112. As shown, there is an exponential relationship between the percentage of track length and percentage of distance range. In this example, the measured percentage of distance range can be "X" and the percentage of track length can be "Y," and the percentage of distance range and the percentage of track length unit can be related by an exponential equation, however, it should be clear that this non-limiting example is intended for illustrative purposes only. The ENA 100 can indicate the distance of an object within the distance range by moving the tactile feedback unit 130 to a location along the track 112 that is exponentially related to the distance of the object within the distance range. Referring to FIGS. 3A and 3C, an object that is at D7, which is 25% of the distance range 300 would be indicated on the ENA 100 by the tactile unit (not shown) being positioned at position 320, which is at approximately 35% of the track length. An object that is at D10, which is at 50% of the distance of the distance range 300 would be indicated on the ENA 100 by the tactile feedback unit being positioned at position 322, which is at approximately 65% of the track length. An object that is at D13, which is 75% of the distance range would be indicated on the ENA 100 by the tactile feedback unit being positioned at position 324, which is at approximately 88% of the track length. This relationship can allow the user to perceive more detailed distance information about objects that are closer to the user, and more general distance information about objects that are further away from the user. The particular exponential relationship used in FIG. 3C is intended as a non-limiting example, and different exponential relationships are specifically contemplated, with D10 being indicated closer to the proximal end 202 or closer to the distal end 204, depending on the particular exponential relationship used.

Figure 3D:
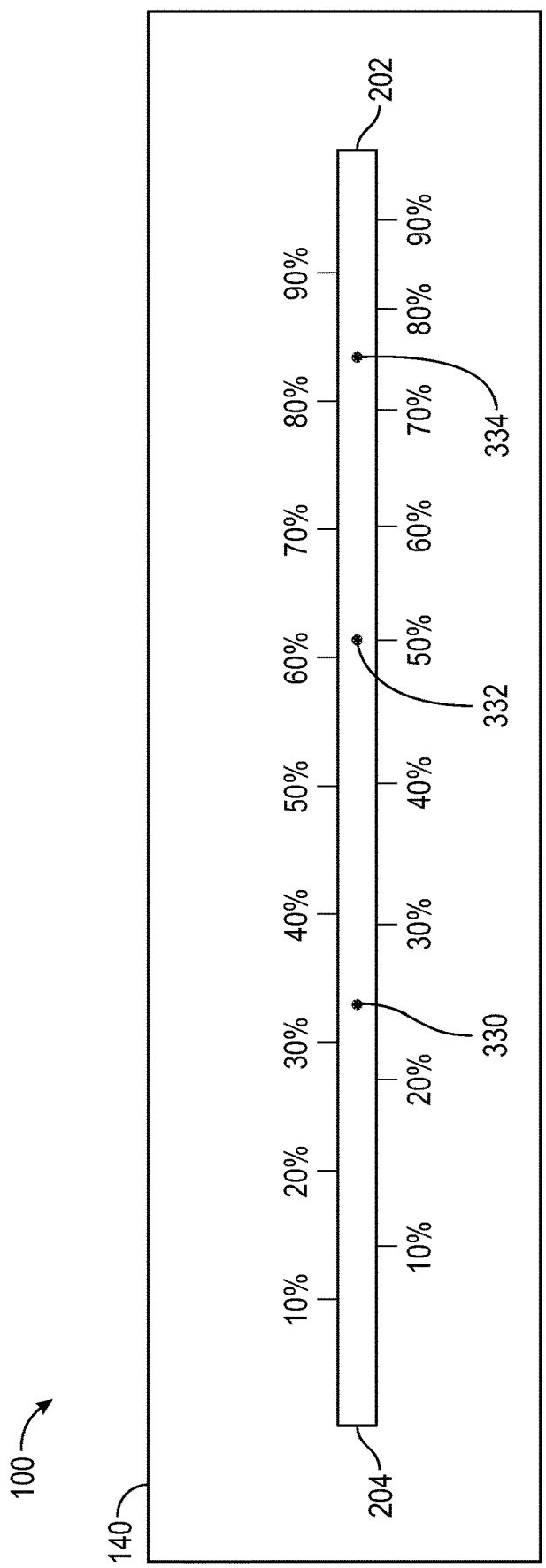
FIG. 3D is a schematic view of an ENA travel path with a polynomial relationship for distances indicated, according to an embodiment.

FIG. 3D is a schematic view of an ENA travel path with a polynomial relationship for distances indicated, according to an embodiment. The length of the track 112 between the proximal end 204 and the distal end 202 can represent the distance range of the ENA. The percentage of the track length is indicated above the track 112, and the percentage of the distance range indicated by the tactile feedback unit at a given location along the track is indicated below the track 112. As shown, there is a polynomial relationship between the percentage of track length and percentage of distance range. In this example, the measured percentage of distance range can be X and the percentage of track length can be Y, and the percentage of distance range and the percentage of track length unit can be related by a multi-order polynomial, however, it should be clear that this non-limiting example is intended for illustrative purposes only. The ENA 100 can indicate the distance of an object within the distance range by moving the tactile feedback unit 130 to a location along the track 112 that is related by a polynomial relationship to the distance of the object within the distance range. Referring to FIGS. 3A and 3D, an object that is at D7, which is 25% of the distance range 300 would be indicated on the ENA 100 by the tactile unit (not shown) being positioned at position 330, which is at approximately 33% of the track length. An object that is at D10, which is at 50% of the distance of the distance range 300 would be indicated on the ENA 100 by the tactile feedback unit being positioned at position 332, which is at approximately 61% of the track length. An object that is at D13, which is 75% of the distance range would be indicated on the ENA 100 by the tactile feedback unit being positioned at position 334, which is at approximately 83% of the track length. This relationship can allow the user to perceive more detailed distance information about objects that are closer to the user, and more general distance information about objects that are further away from the user. The particular polynomial relationship used in FIG. 3D is intended as a non-limiting example, and different polynomial relationships are specifically contemplated, with D10 being indicated closer to the proximal end 202 or closer to the distal end 204, depending on the particular polynomial relationship used. In various embodiments, the relationship between the measured distance and the location of the tactile feedback unit can be directly proportional, or can be related by an exponential equation, a polynomial equation, or various other relationships.

In some embodiments the ENA can be adjustable. An ENA can have various controls in a control area that can include one or more controls to adjust the minimum distance and/or adjust the maximum distance of the distance range. An ENA can have one or more controls to adjust between a fixed relationship, a polynomial relationship, and/or an exponential relationship between the object distance and the tactile feedback unit location, and/or adjust the nature of an exponential relationship to be more or less exponential, or adjust the nature of a polynomial relationship to suit a user, etc.

Figure 4:
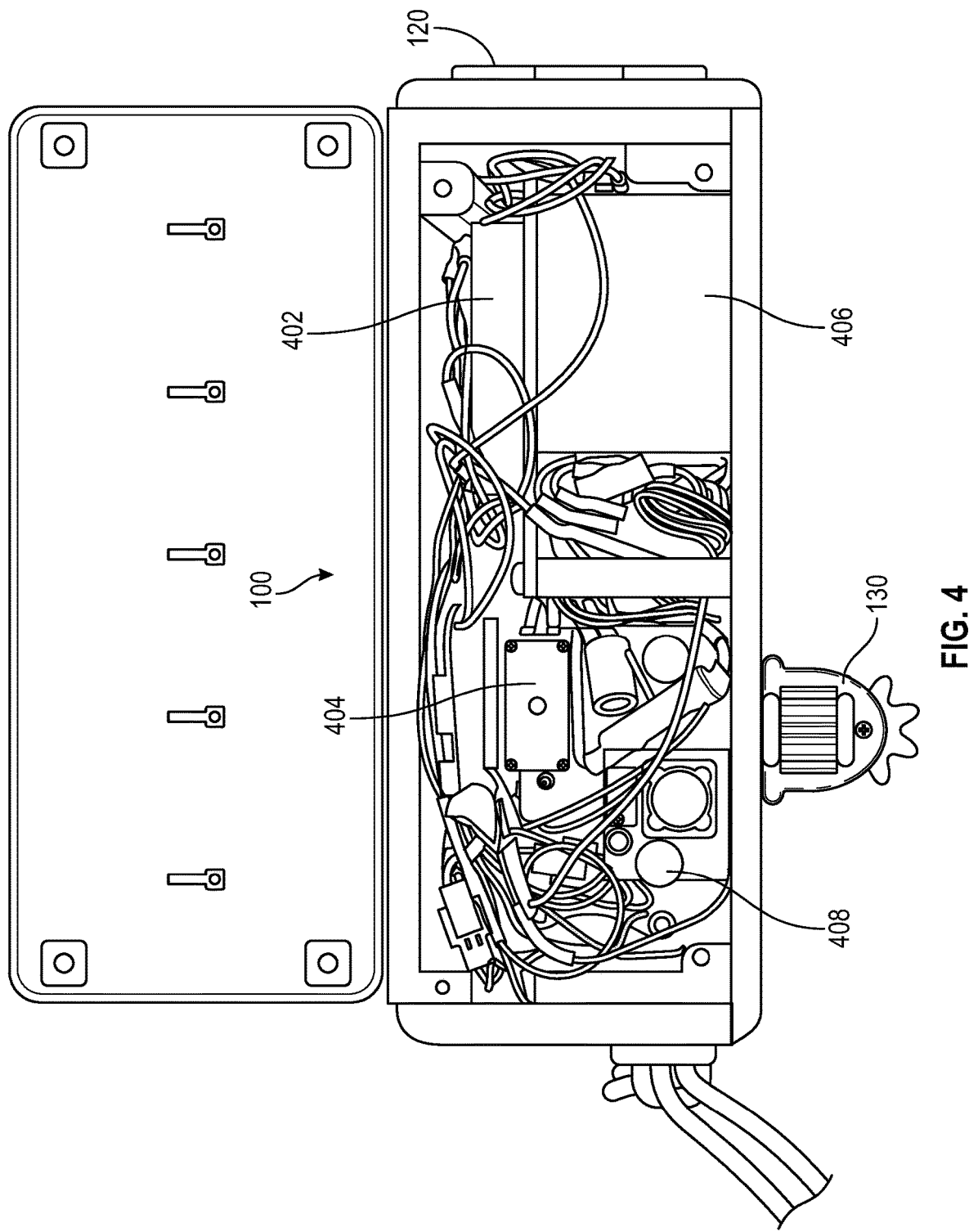
FIG. 4 is a top view of the ENA of FIG. 1, shown with the side removed and internal components exposed, according to an illustrative embodiment.

FIG. 4 is a top view of the ENA of FIG. 1, shown with the side removed and internal components exposed, according to an illustrative embodiment. An ENA 100 can have a processor 402, a servo motor 404, a battery pack 406, and a power management system 408. The range finding unit 120 can be in communication with the processor 402, so that the processor 402 can receive the distance data collected by the range finding unit 120. The processor 402 can be in communication with the servo motor 404, so that the processor 402 can control the movements of the servo motor 404. The servo motor 404 can be operatively connected to the tactile feedback unit 130, so that the servo motor 404 can move the tactile feedback unit along the track. In an embodiment, a pulley system can be used to connect the servo motor to the tactile feedback unit, so that the servo motor can move the tactile feedback unit, but it should be clear that other mechanical linkages could be used. The processor can control the servo motor to move the tactile feedback unit so that the tactile feedback unit can communicate to the user the distance measured by the range finding unit 120. The processor 402 can have various modules that can modify ranging data supplied to the processor 402. These modules can include at least one filtering module that can include selective filters, an averaging module, a scaling module, and a range bounding module for range data supplied from the range finding unit 120 and processed by the processor 402. These modules can be designed to allow a predetermined amount of servo back and forth motion, called scatter, to help indicate the material nature of a target object that an ENA may be pointed at. Due to the nature of sound, smooth surfaces offer clean reflections and may result in minimal or no scatter as presented by the servo 404. This may translate to a steady position of the tactile feedback unit 130. Such a steady position relates to the distance to a target. Absorptive surfaces like clothes offer an intermittent reflection of sound and that can result in a moderate scatter as presented by the tactile feedback unit 130. A user can interpret such scatter in the movement of the tactile feedback unit as it relates to the surface quality and distance parameters. For a very rough surface, like a cluttered desktop, the user could detect a large degree of scatter in the tactile feedback unit. Many levels of scatter may be discernable by a user, enabling them to distinguish between many different types of target objects.

The battery 406 can supply power to the range finding unit 120, the processor 402, and the servo motor 404. The power management system 408 can include a battery charge control and a voltage regulator system. The power management system 408 can help with powering the internal components of the ENA 100 and can help with charging the ENA. The power management system can be connected to various internal components that can include the range finding unit 120, the processor 402, the servo motor 404, the battery 406, and the charging system, explained below.

Figure 5:
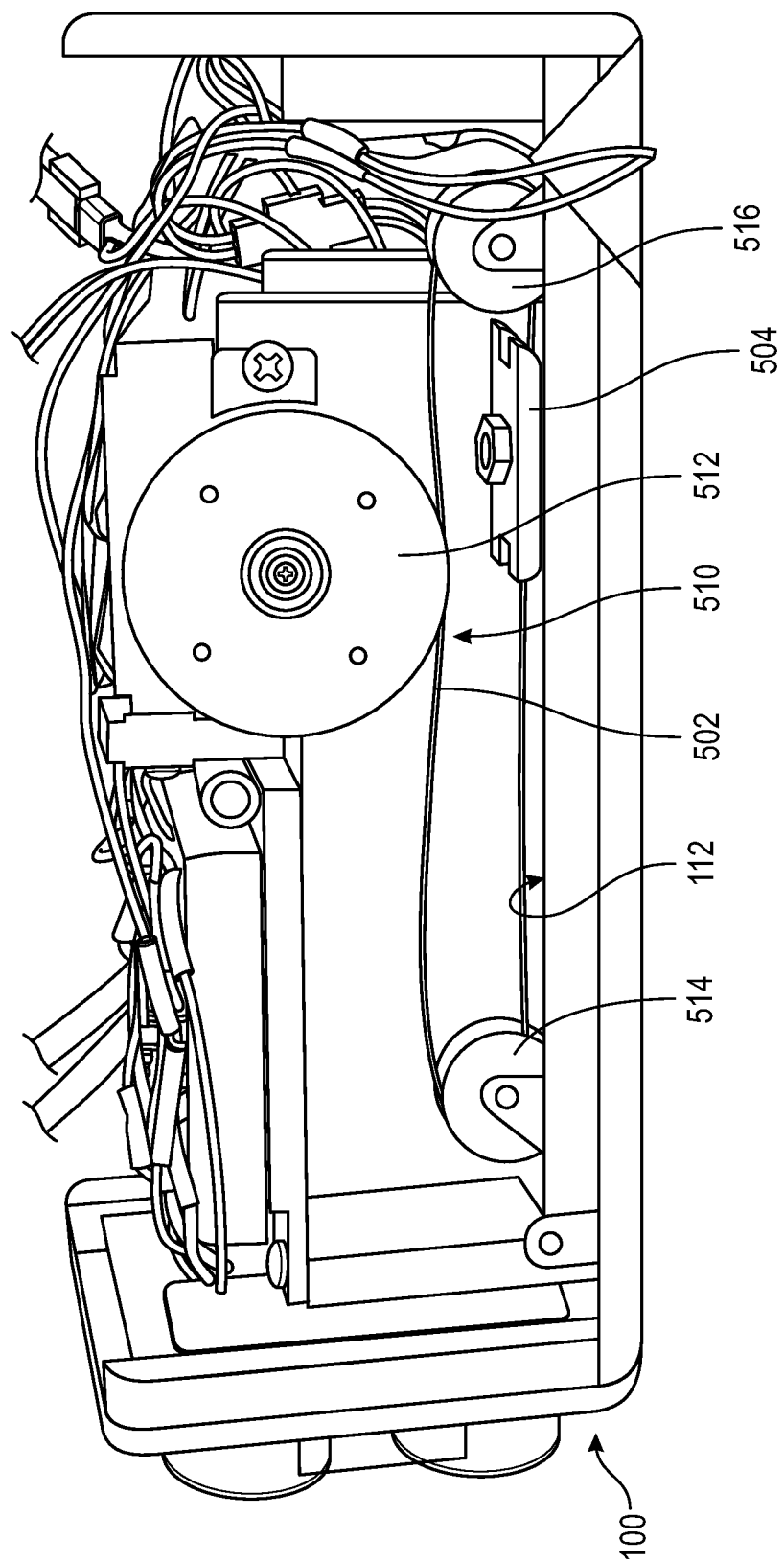
FIG. 5 is a bottom view of the interior of an ENA showing a pulley system connecting the tactile feedback unit to a servo motor, according to an illustrative embodiment.

FIG. 5 is a bottom view of the interior of an ENA showing a pulley system connecting the tactile feedback unit to a servo motor, according to an illustrative embodiment. An ENA 100 can use a cord 502 and a pulley system 510 to move the tactile feedback unit. The ENA 100 can have a tactile feedback unit base 504 that can reside within the outer case of the ENA 100. The tactile feedback unit base 504 can be connected to the tactile feedback unit through the track 112. The cord 502 can be a monofilament, string, chain, or other appropriate material. The cord 502 can be affixed to the tactile feedback unit base 504. The pulley system 510 can include a drive pulley 512, a distal pulley 514, and a proximal pulley 516. The drive pulley 512 can be operatively connected to the servo motor. The cord 502 can be wrapped around the distal pulley 514, the drive pulley 512, and the proximal pulley 516. The cord 502 can be wrapped around the entire circumference, or a portion of the circumference, of the drive pulley 512 to maximize the friction grip between the drive pulley 512 and the cord 502. The friction between the drive pulley 512 and the cord 502 allows the drive pulley 512 to move the cord 502 when the drive pulley 512 turns. When the drive pulley 512 moves the cord 508 through the pulley system 510, the cord 502 moves the tactile feedback unit base 504. Because the tactile feedback unit base 504 is connected to the tactile feedback unit through the track 112, movement of the tactile feedback unit base 504 causes movement of the tactile feedback unit.

When the servo motor turns the drive pulley 512, the cord moves the tactile feedback unit along the track 112 to where the processed servo position code specifies. By way of non-limiting example, when the drive pulley 502 turns in a clockwise direction, as shown in FIG. 5, the cord pulls the tactile feedback unit base 504 towards the proximal pulley 516, which moves the tactile feedback unit towards the proximal end of the track 112. Because the drive pulley 502 can be operatively connected to the servo motor, movement of the servo motor can cause movement of the tactile feedback unit. It should be clear that alternate arrangements of pulley system 510 are specifically contemplated, and do not change the spirit of the design. By way of non-limiting examples, a pulley system 510 could have more than three pulleys, or a pulley system could have only two pulleys with a drive pulley in the proximal or distal pulley location. The example shown in FIG. 5 is provided for illustrative purposes only.

Figure 6:
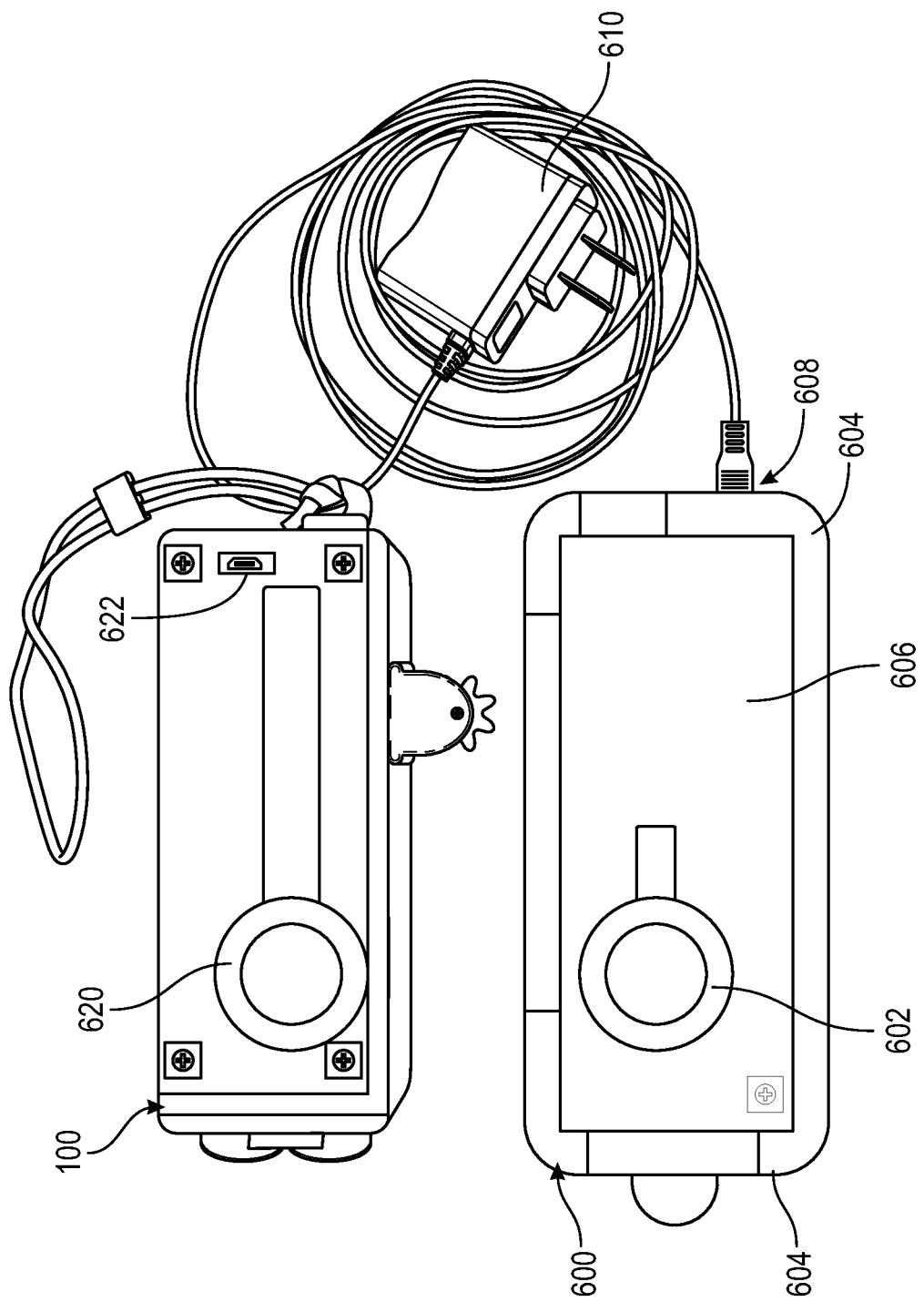
FIG. 6 is a perspective view of the ENA of FIG. 1, along with an exemplary charging station for the ENA, according to an illustrative embodiment.

FIG. 6 is a perspective view of the ENA of FIG. 1, along with an exemplary charging station for the ENA, according to an illustrative embodiment. The ENA 100, shown from the charging side, and the charging unit 600, shown from a top view, can have corresponding charging mechanisms. The ENA 100 can be charged through wireless induction charging, as will be understood by one skilled in the art. A charging station 600 can have a wireless induction charger coil 602, and the ENA 100 can have a wireless induction charging coil 620. In alternate embodiments, the ENA and the charging station can have metal pins, or other means for providing a charge from the charging station to the ENA, as will be understood by one skilled in the art. The charging station can have side rails 604 that can define a cradle 606 on the top of the charging station 600. The cradle 606 can be sized to accommodate the ENA 100 when the ENA 100 is set on the charger. When the ENA 100 is set on the charger, the charging mechanisms can be aligned so that the charger 600 can provide a charge to the ENA 100. The charging station 600 can have a power inlet port 608 that can be in communication with the charging mechanism of the charging station. Power can be provided to the charging station through a plug for a wall socket 610, through a USB plug, or through any means for providing electricity to a charging device, as will be understood by one skilled in the art.

In various embodiments, the ENA 100 can also have a charging port 622 that can be a USB port, micro USB port, or other design that allow the ENA 100 to be plugged in to a power source to charge the battery. The charging port 622 can allow the ENA 100 to be charged while away from home, so that the user can recharge the ENA 100 without the need to carry the induction charging unit 600 while away from home.

Figure 7:
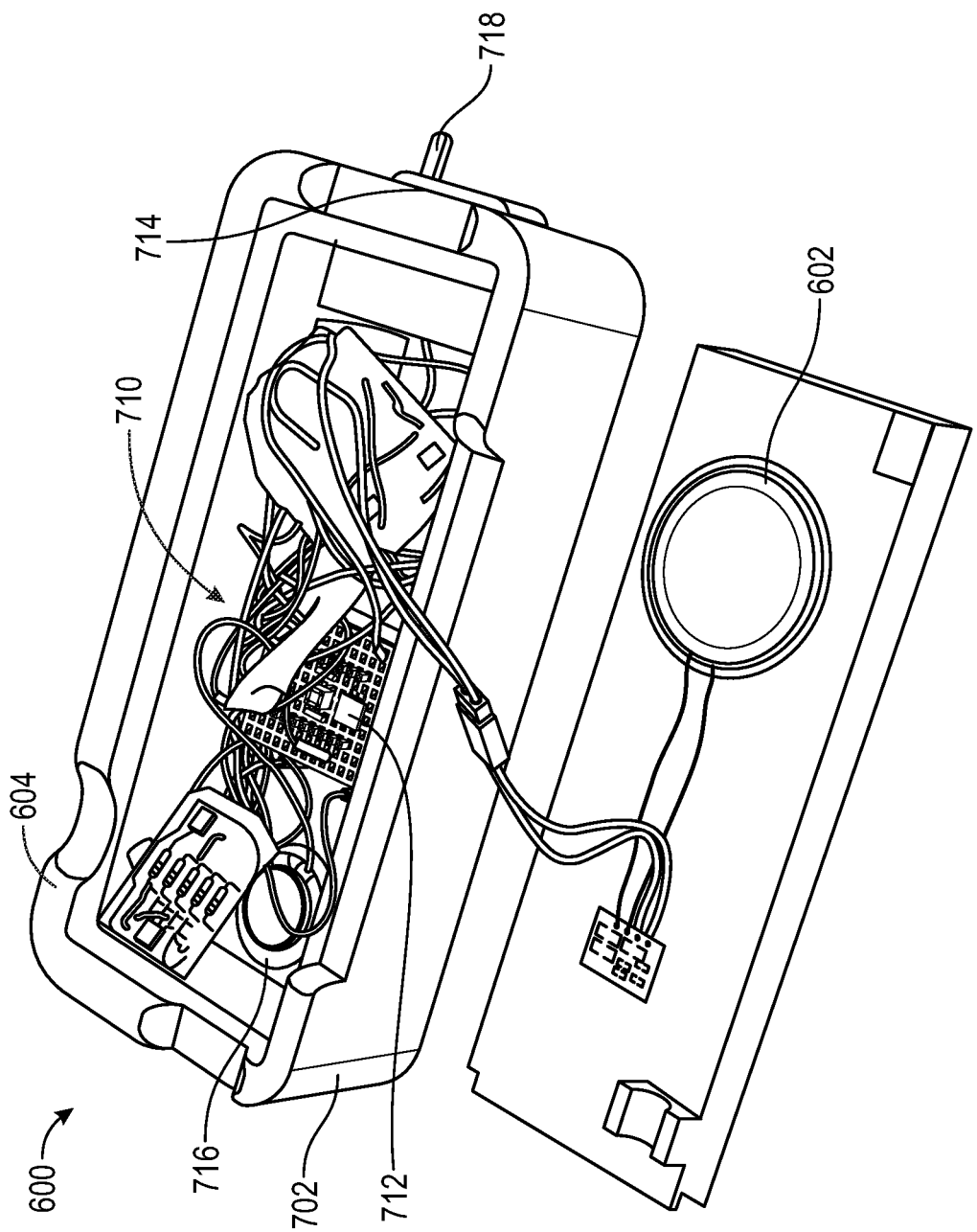
FIG. 7 is a perspective view of the ENA charging station of FIG. 6, shown with the top removed and internal components exposed, according to an illustrative embodiment.

FIG. 7 is a perspective view of the ENA charging station of FIG. 6, shown with the top removed and internal components exposed, according to an illustrative embodiment. The ENA charging station can have a homing system built into the ENA charging station that can detect ultrasonic emissions of the ENA, and can sound a chime, beacon, or other sound when it detects the ultrasonic emission of the ENA. The charging station 600 can have an outer case 702, and a homing system 710 that can include a homing processor 712, a homing microphone 714, a homing speaker 716, and a door 718. The homing microphone 714 can detect range finding emissions from the speaker 122 of the range finding unit 120. The homing microphone 714 can be in communication with the homing processor 712, and the homing processor 712 can verify that the ultrasonic emission detected by the homing microphone 714 is from the speaker 122 of the range finding unit 120. The homing processor 712 can be in communication with the homing speaker 716 of the charging station 600, and the processor 712 can direct the speaker 716 to make a homing chime that can assist a blind person to find the charging station. When the charging station receives the range finder emissions of the ENA unit, the charging station can make a homing chime or other sound to assist a blind person in locating the charger. The charging station can have a door 718 over the microphone 714, so that the door can be used to adjust the response sensitivity of the microphone 714. The door 718 can be placed in a continuum of positions ranging from open to closed, so that the sensitivity of the homing chime response can be modulated. The homing system 710 can also have a user-operated control that can be on the outer case 702, so that the user can adjust the sensitivity by a dial or other control mechanism.

A homing system 710 can also exist separate from a charging station. A homing system can detect ultrasonic emissions of the ENA, and can sound a chime, beacon, or other sound when it detects the ultrasonic emission of the ENA. A user can have multiple homing systems, and different homing systems can have different chimes, tones, or other sounds. The homing system can have user-variable chimes, tones, or other sounds, so that a user can set different homing systems in different locations to produce different sounds. A user can have a different homing system with different sounds located in various key locations to assist a blind user in finding those key locations that can include a bathroom, a bedroom, a kitchen, a front door, or other location. A homing system can also be placed on the exterior of a user's home to assist a user in identifying the location of the user's home without the need for counting steps or other compensatory methodologies often employed by the blind. A homing system may have components that can be spatially separated, such as a small receiving microphone that can be placed discretely for example near a front doorknob or on a mailbox, and a separate speaker unit that can be placed nearby, or even plugged in within the home and placed near a front window.

An ENA can also have an ENA homing system. A charging station can emit a sound or signal that can be an ultrasonic signal, and the microphone 124 of the ENA can detect the signal. The processor of the ENA can determine if the signal detected by the microphone is from the charging station, based on the frequency or other characteristic of the signal, and can cause the ENA to make a homing sound that can be chimes or other sound if the signal is from the charging station. Similarly, any of a number of homing systems placed throughout the home, as described above, can be used to trigger an ENA to produce a homing sound. Any of these homing systems can have a button or other control to cause the homing system to emit the signal to the ENA so that the ENA will produce a homing sound. In various embodiments, the ENA can be programmed to produce a homing sound based on other triggers that can include, for example, recognition of a particular spoken word, vocal pitch, pattern of hand claps, or other triggers that can be produced by the user. The ENA can be programmed to respond to a trigger produced by a user by making a homing sound that can assist the user in locating the ENA. In an embodiment, an ENA can produce a homing chime after a predetermined period of inactivity. The predetermined period of inactivity that induces a homing chime can be 30 seconds. The automatic homing chime after a predetermined period of time can help a blind user find the ENA if the blind user has dropped the ENA or otherwise set it down.

Figure 8:
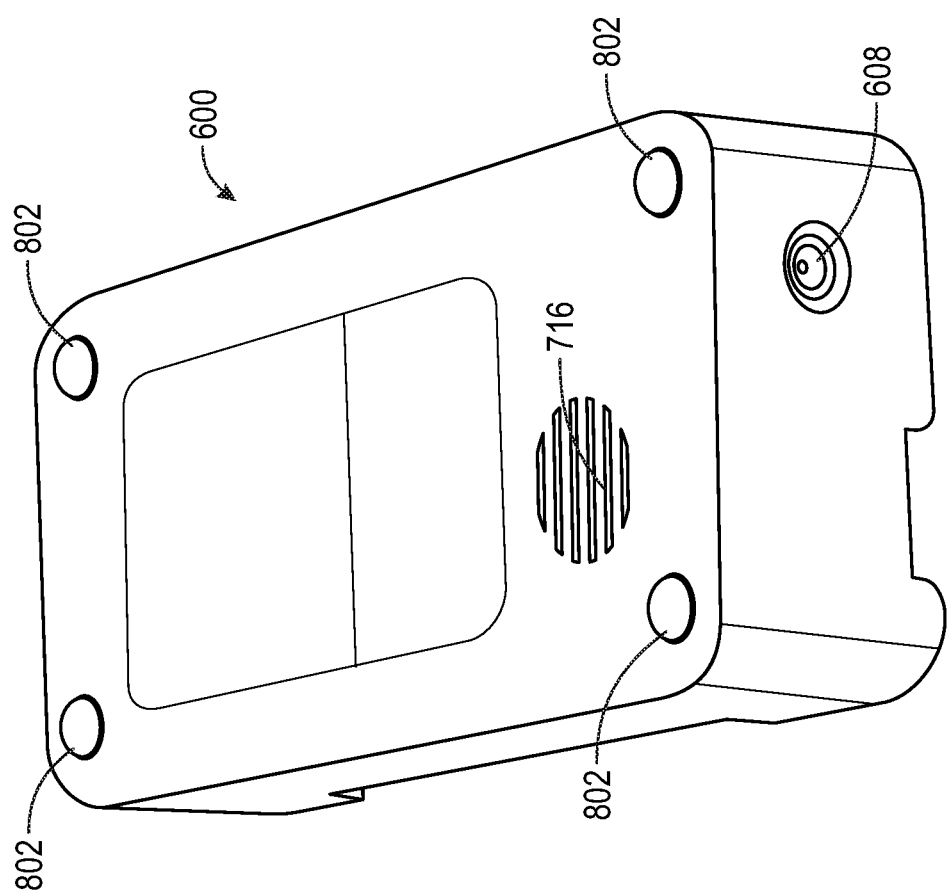
FIG. 8 is a perspective view of the bottom of the exemplary ENA charging station of FIG. 6, according to the illustrative embodiment.

FIG. 8 is a perspective view of the bottom of the exemplary ENA charging station of FIG. 6, according to the illustrative embodiment. The charging station 600 can have feet 802 that can be made of a rubber, silicon, or other appropriate material. The speaker 716 of the charging station can be directed upward from the top of the charging station or downward from the bottom of the charging station, so that the homing chime will emit sound similarly in all directions regardless of which side of the charging station the user is facing. The feet 802 can slightly elevate the charging station so that the homing sound from a speaker 716 on the bottom of the charging station can be heard from any angle.

Figure 9:
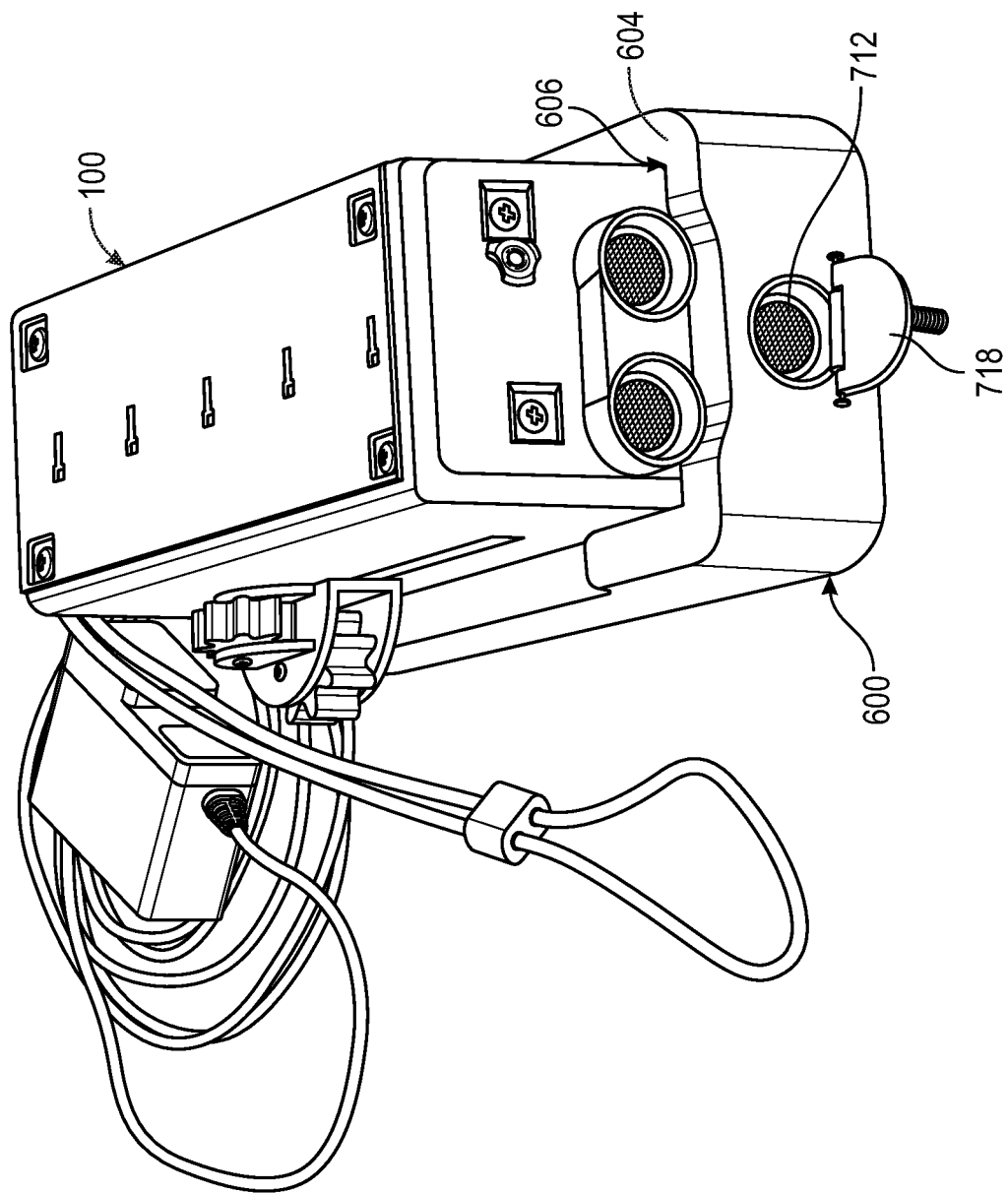
FIG. 9 is a perspective view of an ENA in a charging position atop a charging station with an attached power adaptor, according to an illustrative embodiment.

FIG. 9 is a perspective view of an ENA in a charging position atop a charging station with an attached power adaptor, according to an illustrative embodiment. As shown in FIG. 9, the ENA unit 100 can rest within the depression 606 formed by the side rails 604 of the charging station 600. Door 718 is shown as a hinged door in a fully open position, however in various embodiments door 718 can be a sliding door, rotating door, or other physical means to limit the reception of microphone 714.

Figure 10:
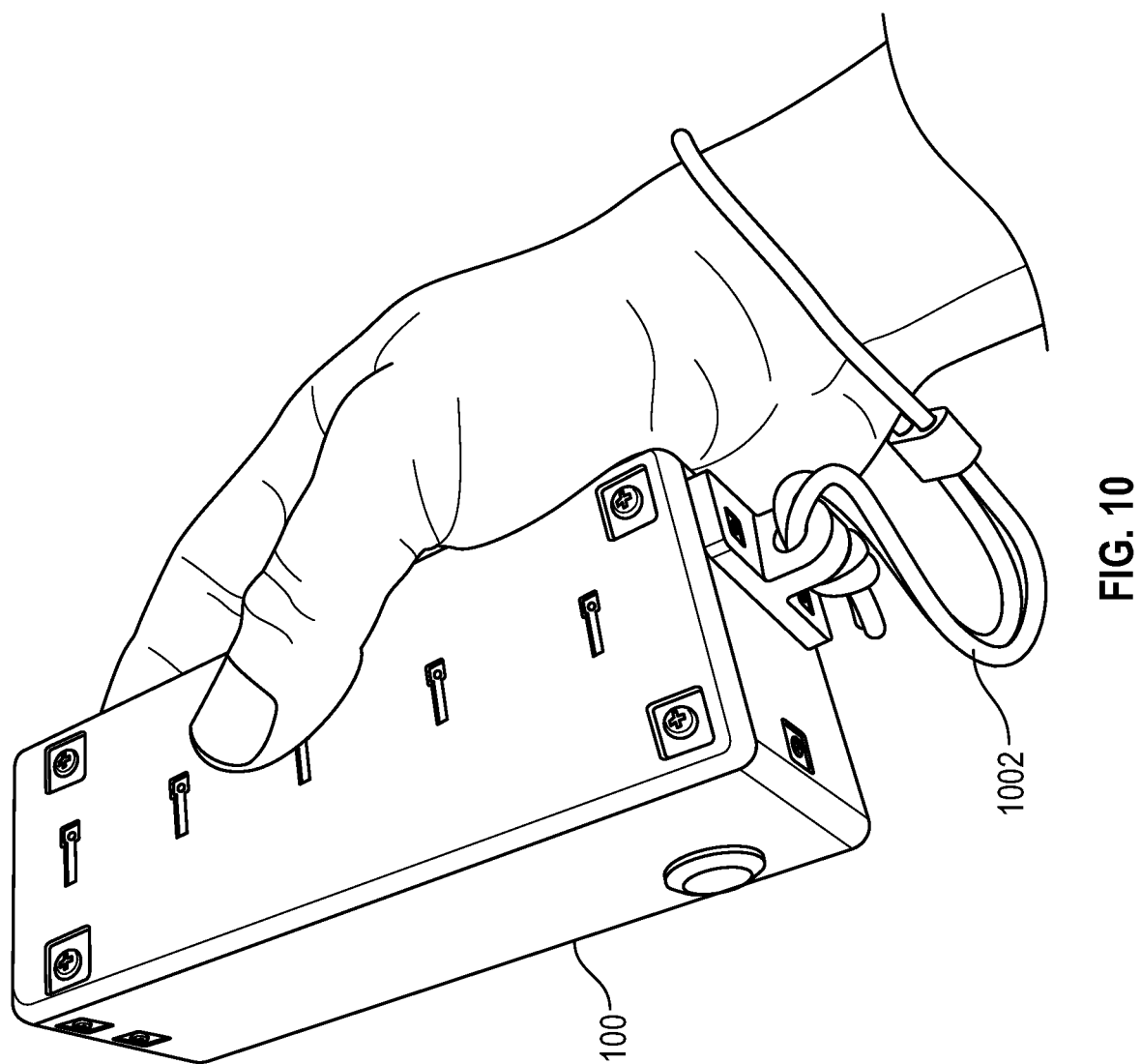
FIG. 10 is a perspective view of an ENA in the hand of a user, showing a first handgrip position with a tactile feedback wheel interfacing with the palm of the user, according to an illustrative embodiment.
Figure 11:
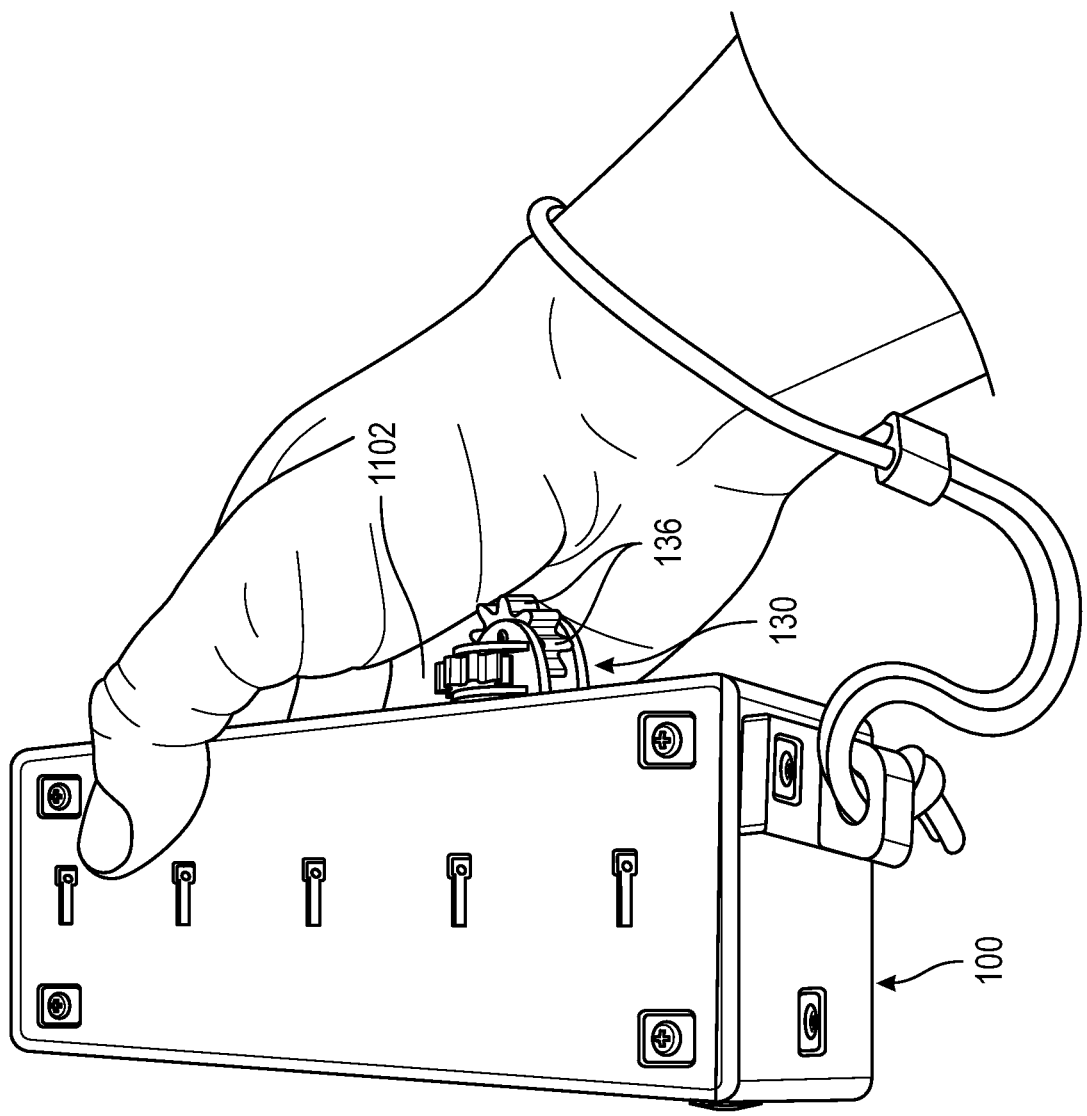
FIG. 11 is a perspective view of the first handgrip position from an alternate perspective, showing the tactile feedback wheel interfacing with the palm of the user, according to an illustrative embodiment.

FIG. 10 is a perspective view of an ENA in the hand of a user, showing a first handgrip position with a tactile feedback wheel interfacing with the palm of the user, according to an illustrative embodiment. The ENA 100 can have a wrist strap 1002 that can be placed around the wrist of the user, around the neck of a user, attached to the clothing of the user, or otherwise used to keep the ENA 100 near the user if the user sets the ENA 100 down to perform a task with the user's hands. In the handgrip position shown in FIG. 10, the tactile feedback unit can travel along the inside of the user's palm. FIG. 11 is a perspective view of the first handgrip position from an alternate perspective, showing the tactile feedback wheel interfacing with the palm of the user, according to an illustrative embodiment. As shown in FIG. 11, the teeth 136 of at least one tactile feedback wheel can be in contact with the skin of the user, so that the tactile feedback unit can communicate information about an object in front of the ENA. As depicted in FIG. 11, the tactile feedback unit can roll along the palm 1102 of the user.

Figure 12:
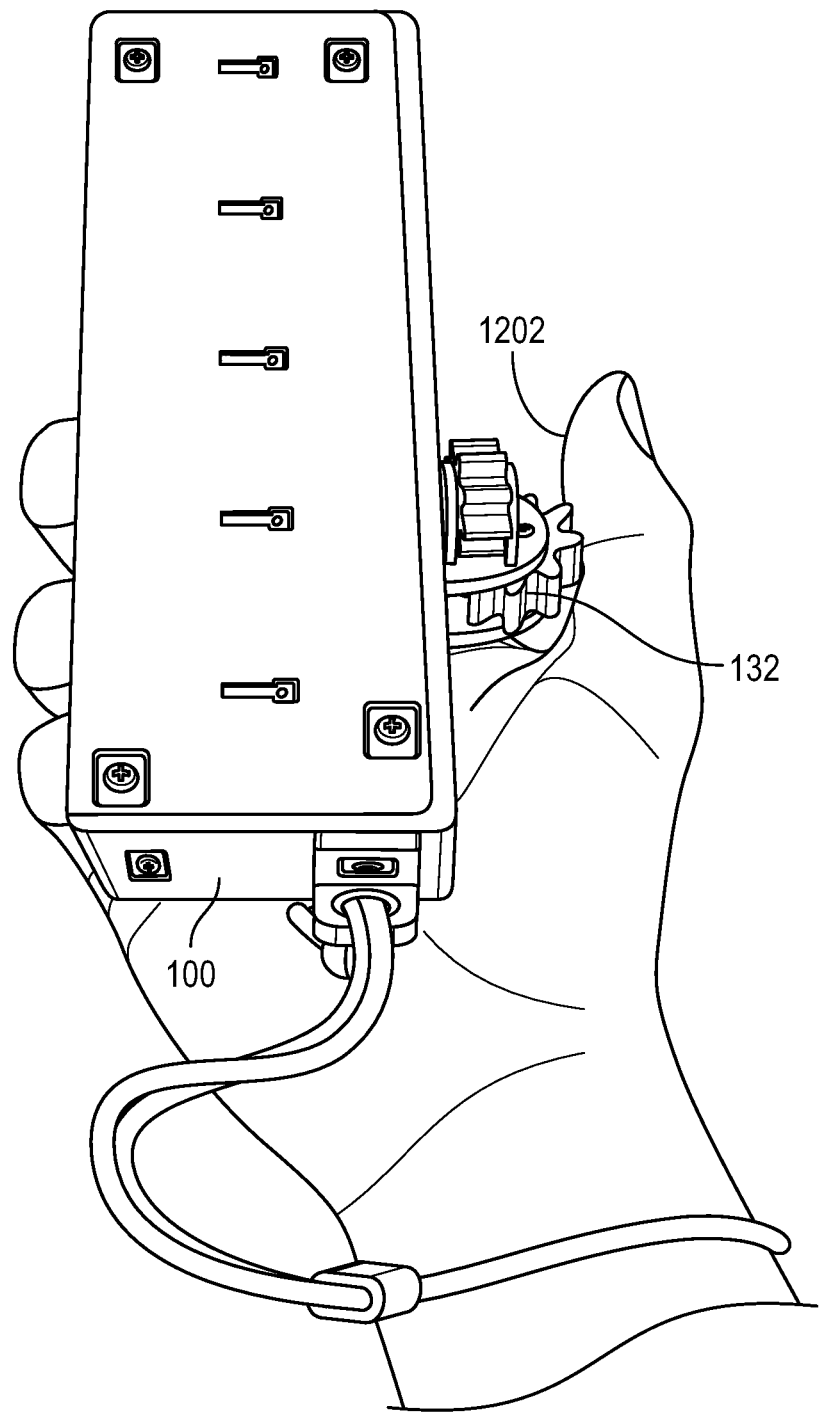
FIG. 12 is a perspective view of a second handgrip position with a tactile feedback wheel interfacing with the thumb of a user, according to an illustrative embodiment.

FIG. 12 is a perspective view of a second handgrip position with a tactile feedback wheel interfacing with the thumb of a user. The ENA 100 can be held in a variety of different positions with a variety of different handgrips, so that the hand of the user does not get tired from gripping the ENA 100 with the same grip in the same position for extended periods of time, and so that the user can vary the location where the ENA contacts the user's skin. By varying the location of contact, the user can avoid having the tactile feedback unit travel over the same area of skin over extended periods of time. FIG. 12 shows another of many different ways the user can hold an ENA 100 so that the tactile feedback unit 130 can provide feedback to different areas of the user's skin. As shown in FIG. 12, at least one of the tactile feedback wheels 132 can roll along the inner surface of the user's thumb 1202 in the depicted handgrip.

Figure 13:
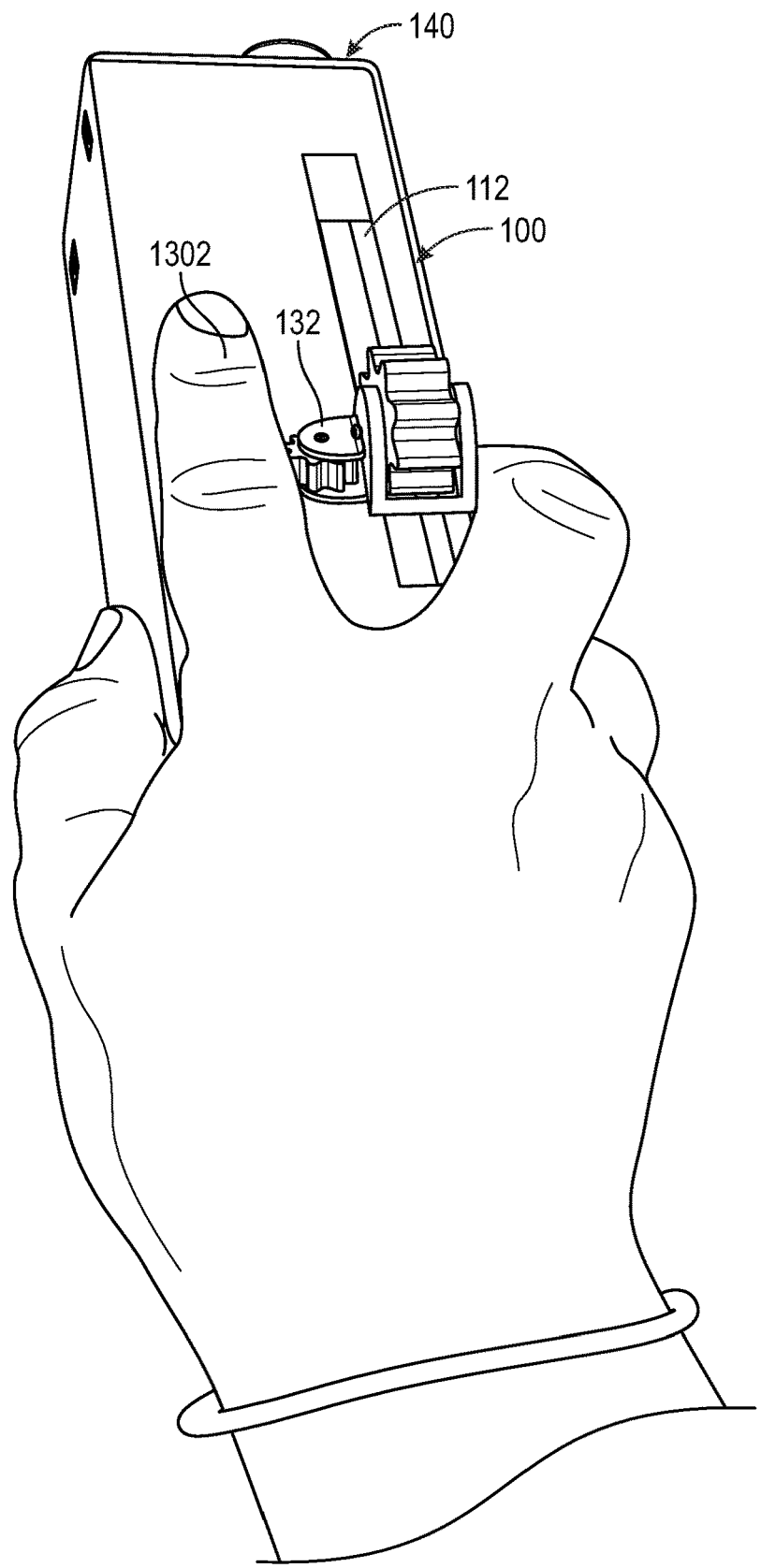
FIG. 13 is a perspective view of a third handgrip position with a tactile feedback wheel interfacing with the side of an index finger of the user, according to an illustrative embodiment.

FIG. 13 is a perspective view of a third handgrip position with a tactile feedback wheel interfacing with the side of an index finger of the user. As shown in FIG. 13, the user can hold an ENA 100 so that at least one of the tactile feedback wheels 132 can travel along the side of a user's finger 1302. FIGS. 10-13 are not intended to be an exhaustive representation of the various handgrips and points of contact that can be utilized by a user, but are intended to illustrate that an ENA can be held and used in a wide variety of positions, and can provide distance information to a user through a number of different contact areas on the user's skin. The palm, finger, or thumb is targeted for the contact with the tactile feedback unit due to the inherent sensitivity of this region of human anatomy. An ENA with multiple feedback wheels can improve the variety and ease with which a user can vary the handgrip and areas of contact, because the multiple wheels allow the tactile feedback unit to be positioned in a number of different orientations relative to each other. A user can hold the ENA 100 in the user's hand in various orientations and can point the front side 140 at an object. The tactile feedback unit 130 can move along the track 112 to communicate to the user the distance between the ENA 100 and the object, and the user can receive the distance information through skin that is placed in a variety of locations relative to the track 112.

Figure 14:
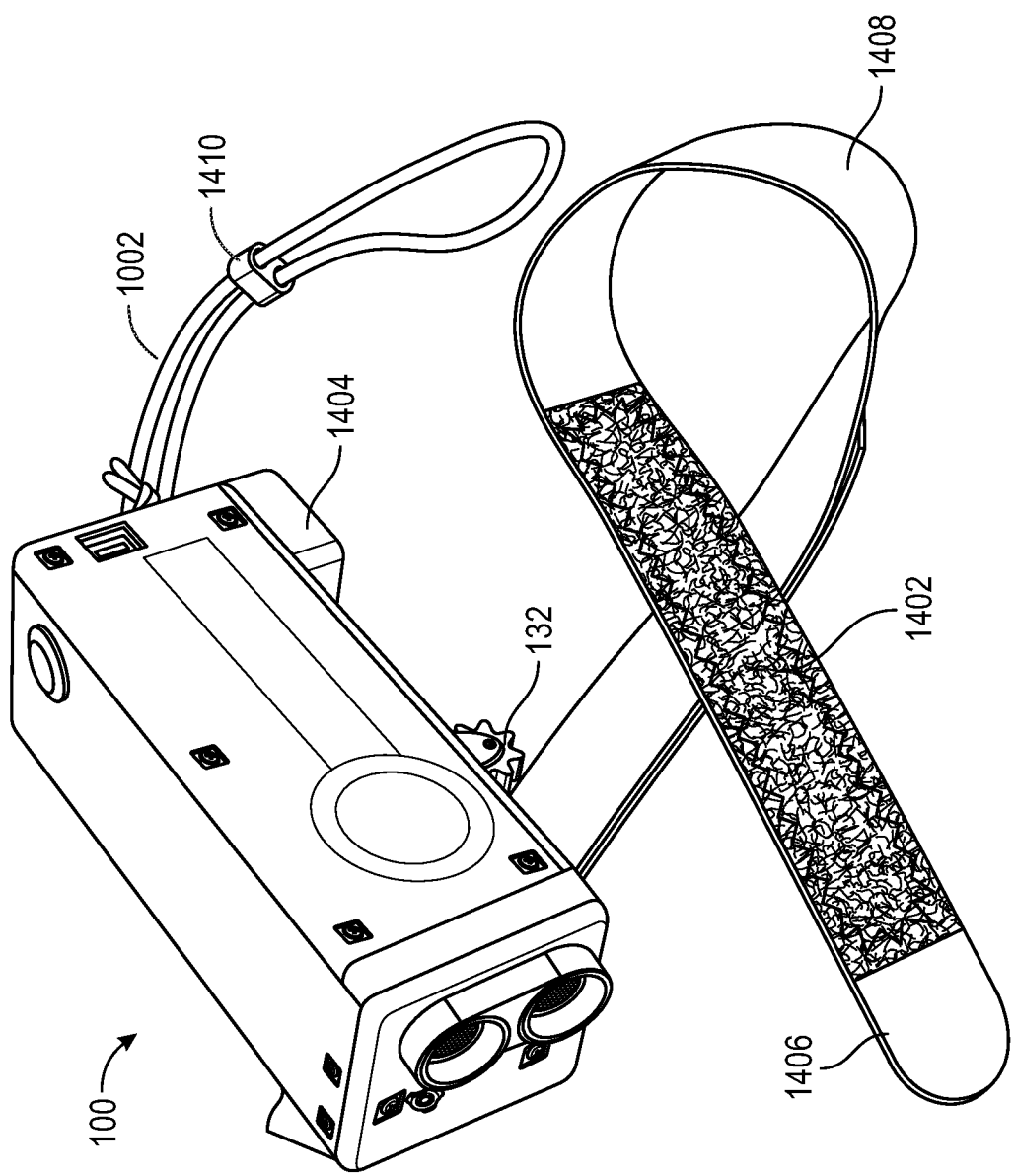
FIG. 14 is a perspective view of an ENA showing various ergonomic features, according to an illustrative embodiment.

FIG. 14 is a perspective view of an ENA showing various ergonomic features, according to an illustrative embodiment. The ENA 100 can have a hand strap 1402 and a wrist rest 1404. The hand strap 1402 can be a flexible material such as a fabric, and can have a hook-and-loop material that can be used to fasten the hand strap around the hand of the user. The hand strap can have a hook material 1406 on an interior surface of the strap, and a loop material 1408 on an exterior surface of the strap, or vice-versa, so that the strap can be wrapped around the hand of the user and secured with the hook and loop tape. In various embodiments, the hand strap could be an elastic material in the shape of a loop, so that the strap can be stretched around the hand of the user without the need for fastening the strap around the hand of the user. The strap can reduce fatigue of the user's hand by reducing the need for the user to continuously hold the ENA 100. Because the strap holds the ENA 100 in place against the hand of the user, the user can feel the tactile feedback without needing to grip the ENA 100 tightly enough to keep it within the user's hand.

The track 112 can be centered down the middle of the ENA between two sides. The wrist rest 1404 can rest against the wrist of the user, and can be held in place against the wrist of the user by the wrist strap 1002. The user can place the wrist strap around the user's wrist, place wrist rest 1404 against the user's wrist, and tighten the wrist strap 1002 by sliding the strap slider 1410 snugly against the wrist to hold the wrist rest 1404 in place against the wrist. The wrist rest 1404 can also hold the ENA 100 in a position so that a portion of the side of the ENA 100 is spaced away from the skin of the user. Spacing at least a portion of the side of the ENA 100 away from the skin of the user can allow the tactile feedback wheel 132 to travel more freely and make isolated contact with the skin of the user, thereby increasing the sensitivity of the contact, or put another way, increasing the user's ability to feel the contact and movement of the feedback wheel 132, because a portions of the side of the ENA 100 is not resting against the user's hand. The wrist rest can also increase comfort and reduce fatigue for the user, because the wrist rest 1404 can help to hold the ENA in an ergonomic position. The hand strap 1402, the wrist strap 1002, and the wrist rest 1404 can work together to hold the ENA 100 comfortably in a desired placement in contact with the user without the user needing to exert muscular effort to hold the ENA 100 in the desired placement, thereby reducing fatigue of the user.

Figure 15:
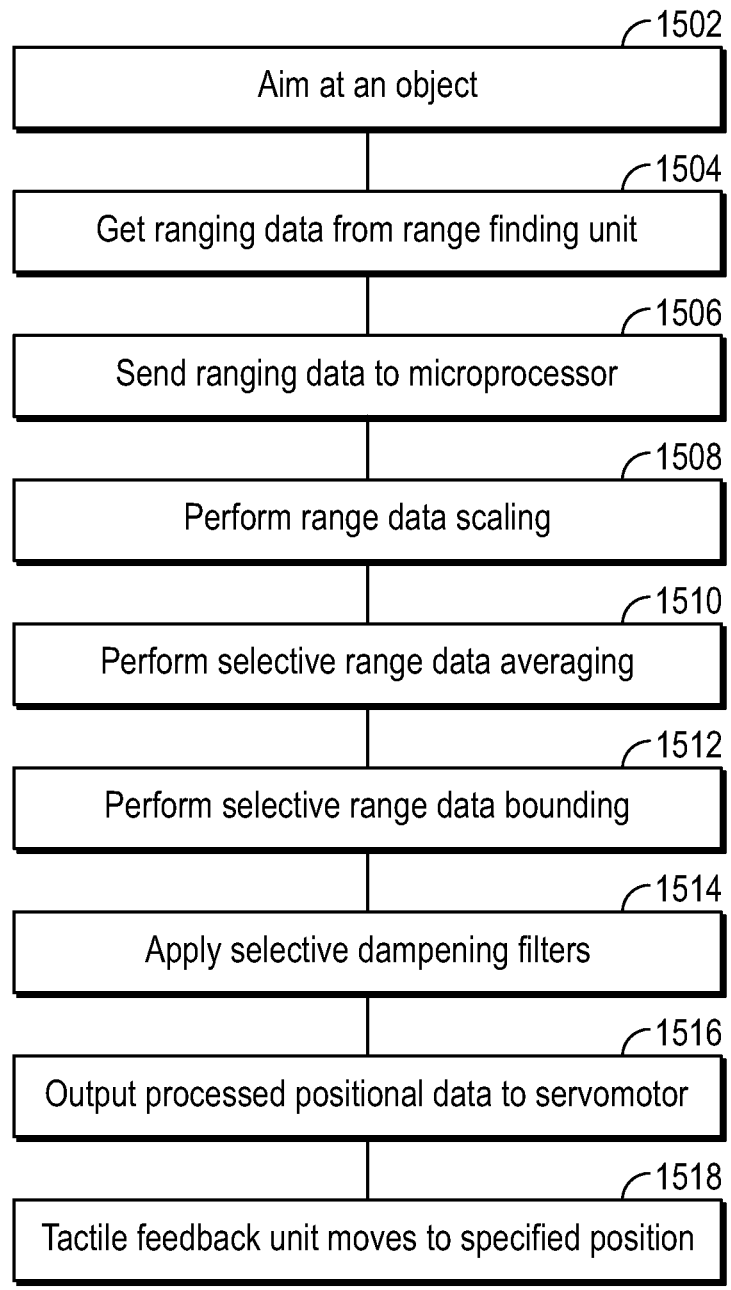
FIG. 15 is a diagram showing the function of an exemplary ENA according to an illustrative embodiment.

FIG. 15 is a diagram showing the function of an exemplary ENA, according to an embodiment. Ranging information can be gathered and processed to result in motion of the tactile feedback unit. At 1502, a user can point the ENA at an object. At 1504, the range finding unit can obtain range data and at 1506 the range finding unit can transfer that range data to the processor. At 1508, the processor can perform scaling of the range data to suit the needs of the servomotor and the range of motion of the tactile feedback unit. At 1510, the processor can perform selective averaging of the scaled range data from 1508 to help smooth out motions of the tactile feedback unit. At 1512 the processor can perform selective range bounding of the processed range data from 1510 to eliminate out-of-range data. At 1514, the processor can apply selective dampening filters to the processed range data from 1512 to further smooth out the motions of the tactile feedback unit. At 1516, the processor can send the final processed positional data to the servomotor. At 1518 the servomotor can initiate motion of the tactile feedback unit. As the servomotor rotates to a position as specified by the processed range data it can move the tactile feedback unit to the predetermined position through the use of a pulley or other mechanical linkage. The process can be repeated continuously to keep the motions of the tactile feedback unit flowing and representative of the distance to a target. The process can allow the user to receive real-time distance information as the user moves through the environment and/or points the ENA in different directions and at different objects.

Figure 16:
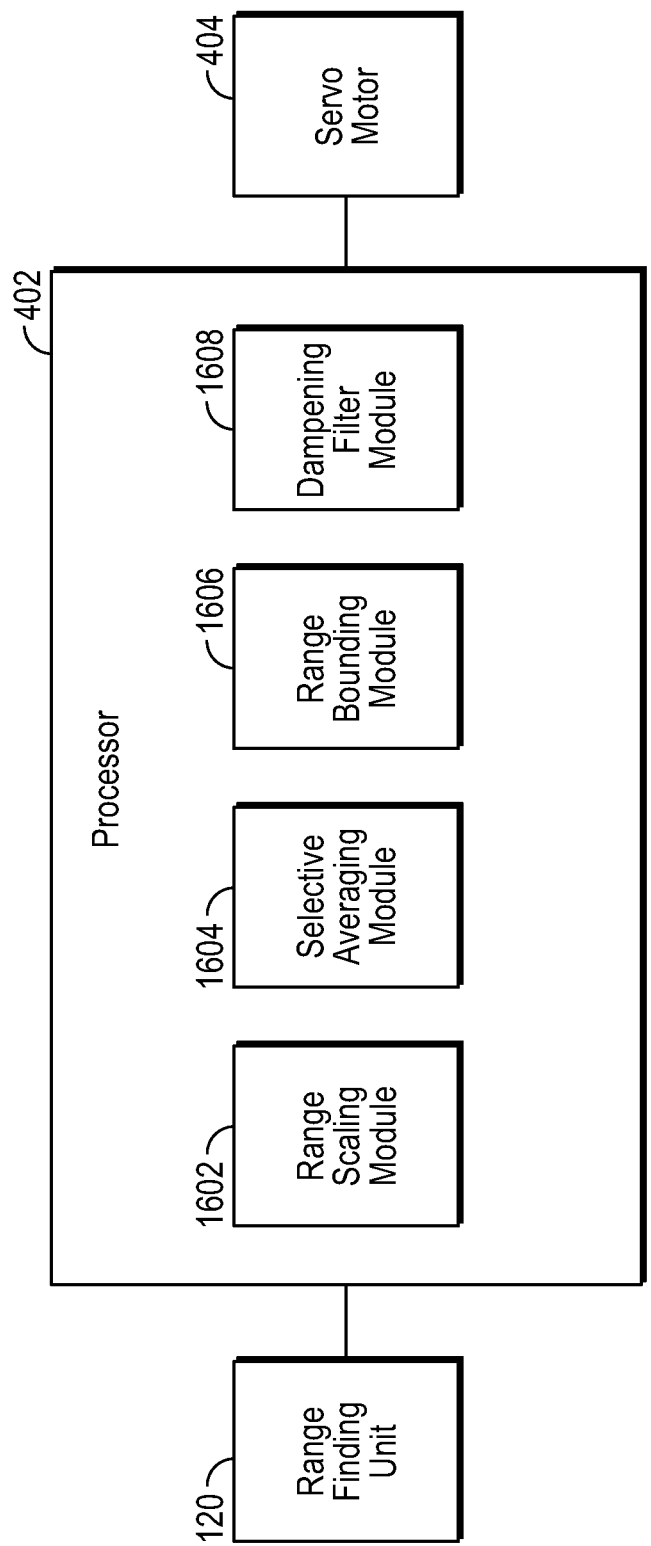
FIG. 16 is a schematic diagram of an exemplary ENA, according to an illustrative embodiment.

FIG. 16 is a schematic diagram of an exemplary ENA, according to an illustrative embodiment. Range finding unit 120 can be in communication with a processor 402. The processor can send a trigger input to the range finding unit 120. The range finding unit 120 can have an output that can be range data in the form of return time to the object, which can be a measure of how long it takes for an ultrasonic tone to travel to the object and back to the ENA. The range finding unit 120 can provide the processor 402 with the distance data collected by the range finding unit 120 about the distance between the range finding unit 120 and an object. The processor 402 can have various modules that can include a range scaling module 1602, a selective averaging module 1604, a selective range bounding module 1606, and/or a dampening filter module 1608.

The range scaling module 1602 can receive the range data as an input. The range scaling module 1602 can perform scaling of the range data to suit the needs of the servomotor and the range of motion of the tactile feedback unit. The range scaling module 1602 can have constants that can be servo code for minimum servo position, servo code for maximum servo position, a specified maximum inch distance to target, and a constant for standard air density. The range scaling module can convert the range data input by a transform that can compensate for standard air density, and can convert return time into inch distance to target. The range scaling module can apply a mathematical formula to the range bound inch distance data that can transform the distance data to processed servo position code that can be bound between minimum servo position and maximum servo position. The mathematical formula can be a second order polynomial, exponential formula, or other mathematical relationship that can enhance the range response for nearer objects. The range scaling module can output processed servo code.

The selective averaging module 1604 can perform selective averaging of the scaled range data to help smooth out motions of the tactile feedback unit. The selective averaging module 1604 can use the current processed servo position code and the last processed servo position code as inputs. The selective averaging module 1604 can have a minimum variation threshold as a constant. When the variation in the servo position code is greater than the minimum variation threshold, the selective averaging module 1604 can average the currently generated servo position code with the previous servo position code. The selective averaging module 1604 can output processed servo position code.

The selective range bounding module 1606 can eliminate data that is outside of the distance range. The selective range bounding module 1606 can have the current processed servo position code, last processed servo position code, and last servo movement direction as inputs. The selective range bounding module 1606 can determine current movement direction based on last and current servo position. If the current movement direction is opposite of the last movement direction, the selective range bounding module 1606 can alter the current servo position to be the same as the last servo position. The last movement direction can be set equal to current movement direction. The range bounding module 1606 can output processed servo position code and the last movement direction.

The dampening filter module 1608 can apply selective dampening filters to further smooth out the motions of the servomotor 404 and tactile feedback unit. The dampening filter module 1608 can have the current processed servo position code and the last processed servo position code as inputs. The dampening filter module 1608 can have a maximum variation threshold as a constant. When the variation in the servo position code is greater than the maximum variation threshold, the dampening filter module 1608 can set the variation between the last servo position code and the current servo position code equal to the maximum variation threshold by reduction of the current servo position code. The dampening filter module 1608 can output processed servo position code.

The processor can be in communication with the servo motor 404, so that the processor can direct the movements of the servo motor 404 based on the range data processed by the processor. The servo motor 404 can have the processed servo position code as an input. Using the servo position code, the servo motor can turn to the specified position, which can result in motion of the tactile feedback wheel. The servomotor can cause the tactile feedback unit to move to a location on the ENA indicative of the distance between the range finding unit 120 and the object.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, in alternate embodiments, the range finding unit can be a laser-based range finder. In alternate embodiments, the angle of measurement can be adjustable by adjusting the protective shield around the range finding unit. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Accordingly, this description is meant to be taken only by way of example, and not to otherwise limit the scope of this invention.

What is claimed is:

1. An Environment Navigation Aid (ENA) comprising:
   a range finding unit that measures a distance between an object and the ENA; and
   a tactile feedback unit with at least one tactile feedback wheel, the at least one tactile feedback wheel including teeth arranged around the wheel, wherein the tactile feedback unit moves along an exterior of the ENA to indicate the distance between the object and the ENA.

2. The ENA of claim 1, wherein the at least one tactile feedback wheel has a central axis that is perpendicular to a direction of travel of the tactile feedback unit.

3. The ENA of claim 2 wherein the at least one tactile feedback wheel comprises at least two tactile feedback wheels.

4. The ENA of claim 3, wherein the central axis of a first wheel is perpendicular to the central axis of a second wheel.

5. The ENA of claim 1, wherein the range finding unit uses ultrasound to measure the distance between the object and the ENA.

6. The ENA of claim 5, wherein the range finding unit comprises:
   a speaker; and
   at least one microphone.

7. The ENA of claim 1, wherein the tactile feedback unit can provide information to the user about the surface texture of an object.

8. The ENA of claim 1, further comprising a homing unit that can make a noise in response to a predetermined stimulus.

9. The ENA of claim 8, wherein the predetermined stimulus is an ultrasonic tone produced by an ENA charging unit.

10. The ENA of claim 1, wherein a location of the tactile feedback unit is directly proportional to the distance between the object and the ENA.

11. The ENA of claim 1, wherein a location of the tactile feedback unit is exponentially proportional to the distance between the object and the ENA.

12. A method for a blind user to navigate an environment comprising:
   pointing a range finding Environment Navigation Aid (ENA) at an object;
   feeling the location of wheels on the tactile feedback unit; and
   determining, based on the location of a tactile feedback unit on the ENA, a distance between the object and the ENA.

13. The method of claim 12, further comprising determining, based on small movements of the tactile feedback unit, the texture of a surface of the object.

14. The method of claim 12, wherein feeling the location of the wheels further comprises feeling the location of teeth on the wheels.

15. An Environment Navigation Aid (ENA) comprising:
   a range finding unit that measures a distance between an object and the ENA; and
   a tactile feedback unit with at least one tactile feedback wheel, wherein the tactile feedback unit can provide information to the user about the surface texture of an object, wherein the tactile feedback unit moves along an exterior of the ENA to indicate the distance between the object and the ENA.

16. The ENA of claim 15, wherein the at least one tactile feedback wheel has a central axis that is perpendicular to a direction of travel of the tactile feedback unit.

17. The ENA of claim 16 wherein the at least one tactile feedback wheel comprises at least two tactile feedback wheels.

18. The ENA of claim 17, wherein the central axis of a first wheel is perpendicular to the central axis of a second wheel.

* * * * *